United States Patent [19]
Batz et al.

[11] Patent Number: 6,117,973
[45] Date of Patent: Sep. 12, 2000

[54] PNA MONOMERS WITH ELECTRON DONOR OR ACCEPTOR

[75] Inventors: Hans-Georg Batz, Tutzing, Germany; Henrik Frydenlund Hansen, Rodovre, Denmark; Henrik Orum, Varlose, Denmark; Troels Koch, Kopenhagen, Denmark; Gary B. Shuster; Bruce A. Armitage, both of Atlanta, Ga.

[73] Assignees: Georgia Tech Research Corp., Atlanta, Ga.; Roche Diagnostics GmbH, Mannheim, Germany

[21] Appl. No.: 08/805,411

[22] Filed: Feb. 24, 1997

[51] Int. Cl.[7] ..................................................... C07K 5/00
[52] U.S. Cl. .............................. 530/300; 435/6; 436/501; 530/350
[58] Field of Search ................. 435/6, 810; 436/501; 530/350; 536/23.1, 24.1, 24.3–24.33, 25.3; 935/77, 78

[56] References Cited

U.S. PATENT DOCUMENTS 5,770,369  6/1998  Meade et al. ............................. 435/6

FOREIGN PATENT DOCUMENTS

WO 92/20703  11/1992  WIPO.
WO 94/25477  11/1994  WIPO.
WO 95/15971  6/1995   WIPO.
WO 96/15270  5/1996   WIPO.

OTHER PUBLICATIONS

Dreyer et al., Proceedings of the National Acad. of Sci (USA), vol. 82, pp 968–972, 1985.
Egholm et al., Nature, vol. 365, pp 566–568, 1993.
Egholm et al., Journal of the American Chemical Society, vol. 114, No. 5, pp. 1895–1897, 1992.
Science, vol. 262, Nov. 12, 1993, Murphy et al., "Long-Range Photoinduced Electron Transfer Through a DNA Helix".
Nature Biotechnology, vol. 14, Mar. 1996, Tyagi et al., "Molecular Beacons: Probes that Fluoresce upon Hybridization".
International Publication No. WO 92/20703 published Nov. 26, 1992.
International Publication No. WO 92/20702 published Nov. 26, 1992.
International Publication No. WO 95/15971 published Jun. 15, 1995.
International Publication No. WO 96/11205 published Apr. 18, 1996.

*Primary Examiner*—Ardin H. Marschel
*Attorney, Agent, or Firm*—Arent Fox Kintner Plotkin Kahn

[57] ABSTRACT

New electron transfer moiety labeled nucleic acid analogue probes are provided that can be used in methods for determining nucleic acids in a sample. The new probes can be prepared using novel monomer subunits in a chemical synthesis route. The nucleic acids can be determined by binding the probe molecules to the nucleic acid and inducing electron transfer within the complex formed. The occurrence of the electron transfer is determined as a measure of the nucleic acid.

9 Claims, 16 Drawing Sheets

```
PNA 1: T C A C Ac A G A C
       | | | |     | | |
PNA 2: A G T G A Do C T G C T T G A C A G T
```
                                        ANALYTE SPECIFIC

ANALYTE

```
PNA 2   A G T G A Do C T G C T T G A C A G T
        | | | | | | | | | | | | | | | | |
        T C A C T X G A C G A A C T G T C A
```
                                    + PNA 1: T C A C Ac A G A C

Fig.2
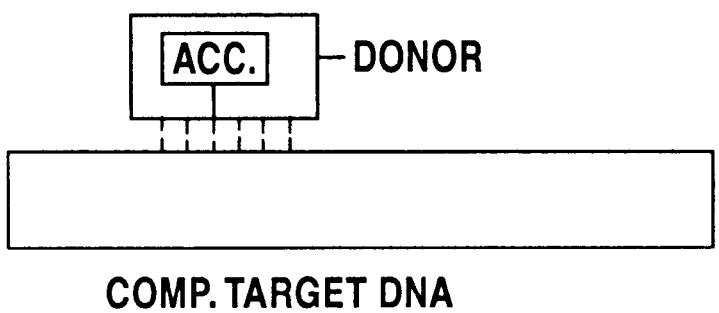
E.T. - DETECTION
COMP. TARGET DNA
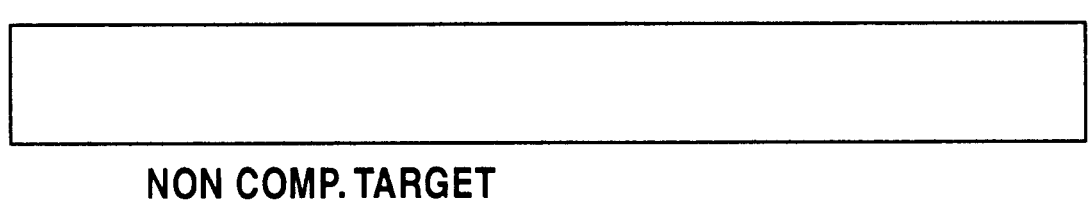
NO E.T.
NON COMP. TARGET

Fig.3
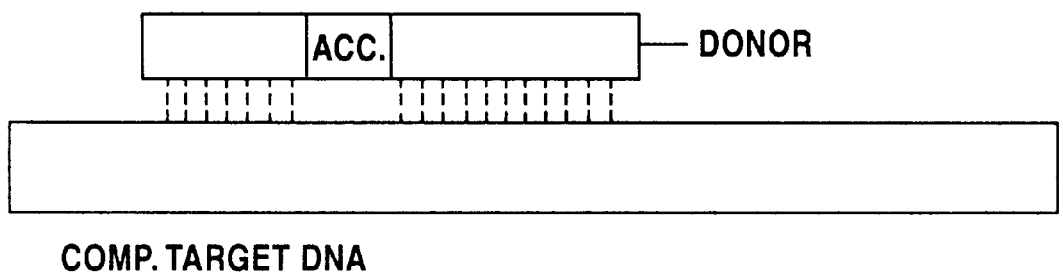
E.T. - DETECTION
COMP. TARGET DNA
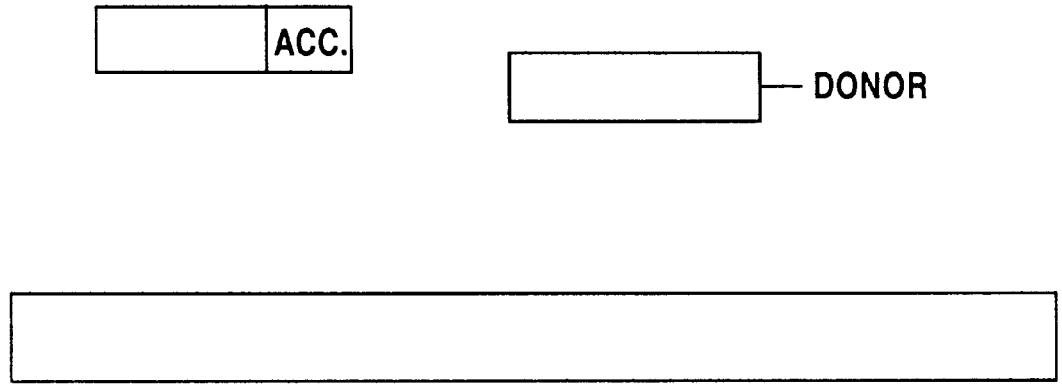
NO E.T.
NON COMP. TARGET

Fig.6

```
                              A
        T C A C Do A G A C  G A     C
        A G T G A  T C T Ac C T     T
                           G
                     |
                     | DNA
                     ↓

```
    PNA 1: T C A C Ac A G A C
           | | | |     | | |
    PNA 2: A G T G A Do C T G C T T G A C A G T
```

ANALYTE SPECIFIC

│ ANALYTE
                          ↓

```
    PNA 2    A G T G A Do C T G C T T G A C A G T
             | | | | | | | | | | | | | | | | | |
        ——   T C A C T X  G A C G A A C T G T C A  ——
```

+ PNA 1: T C A C Ac A G A C

Fig.10
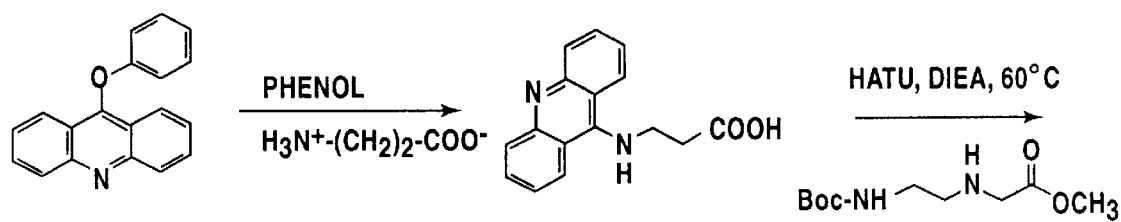
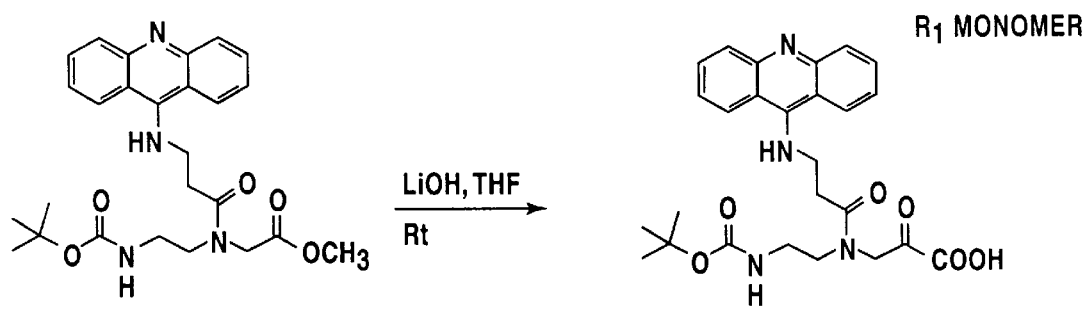

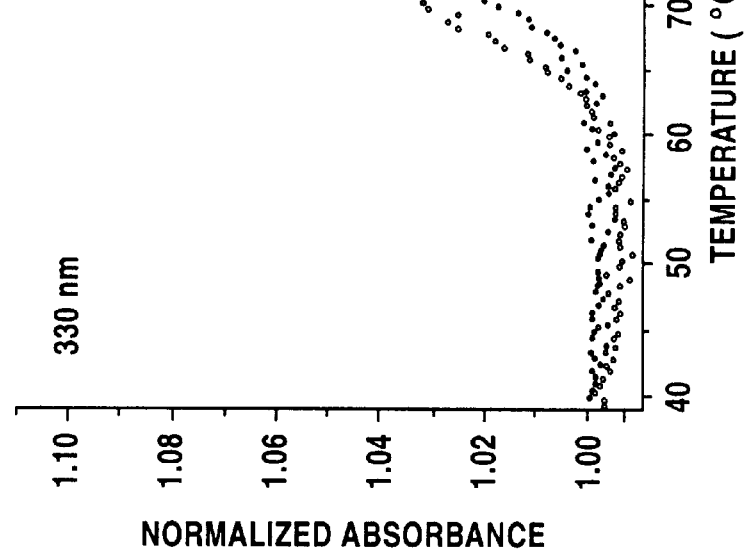
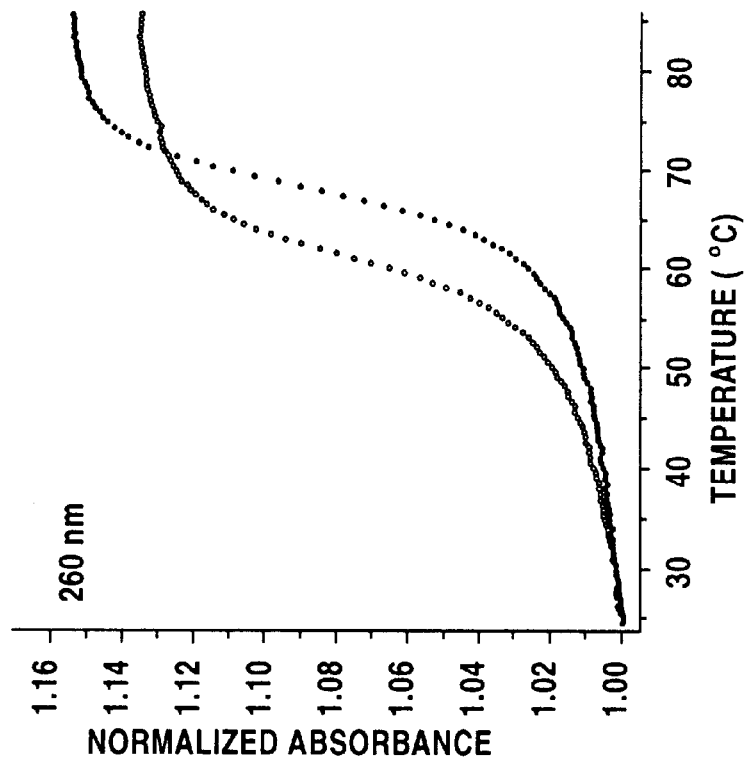

MELTING OF PNA HAIRPINS

MELTING OF PNA/DNA HYBRIDS

ND MONOMERS WITH ELECTRON
DONOR OR ACCEPTOR

The invention of this application was conceived with support from the United States Government, and specifically the National Institutes of Health.

FIELD OF THE INVENTION

The present invention is directed to methods for determining a nucleic acid in a sample with a probe molecule using electron transfer from an electron donor to an electron acceptor. The invention is further directed to compounds useful in such methods and to compounds useful for the preparation of the probe molecules.

BACKGROUND OF THE INVENTION

Determinations of nucleic acids is becoming increasingly important as a tool for diagnosis in the health fields. For example, the presence of nucleic acids from organisms, like viruses, usually not present in the human body, can be determined using probes for the infecting nucleic acids. Further, any changes in the genome which may have a potential influence on the metabolism and the state of health of the individual can be determined. Such changes may have occurred by mutation or other means. Nucleic acid determination has made further progress with the introduction of nucleic acid amplification procedures, like the polymerase chain reaction (PCR).

The presently known nucleic acid assays can be divided into two types, the heterogeneous and the homogeneous assays. In heterogeneous assays, the nucleic acid is determined by binding to a nucleic acid probe which is labeled for detection or by incorporation of labeled mononucleoside triphosphates and subsequent immobilization of the so-labeled nucleic acid to a solid phase. This is preferably done by using a solid phase bound capture probe, a format which provides the advantage that any excess amount of labeled probes or mononucleotides can easily be separated from the solid phase bound labeled nucleic acid. The homogeneous type of nucleic acid assay uses the interference between two labels. In a first method, the two labels are linked together and the event of hybridization initiates cleavage of the linkage between the two labels. (The labels are chosen such that they elicit a signal as soon as they are separated.) In a second method, the distance between the labels is changed by hybridization events. In this case, the labels may be located on one probe or on two separate probes having the capability of hybridizing to the analyte nucleic acid such that the labels can interact with each other.

Electron transfer between donors and acceptors is to be subdivided into two categories. In the first category, the donors (Do) and acceptors (Ac) are bound to the DNA duplex by non-covalent forces, such as van der Waals', electrostatic and hydrogen bonding. In the second class are systems where Do and Ac are covalently linked to the DNA. The earliest demonstration of the first approach was reported by Fromherz and Rieger in 1986, who studied photointitated electron transfer (PET) from intercalated ethidium to surface-associated methyl viologen (romherz, P.; Rieger, B. J. Am. Chem. Soc. 1986, 108, 5361). Electron transfer products were demonstrated by direct observation of the reduced viologen acceptor. However, no special effect of the DNA, other than to provide a high effective concentration of the donor and acceptor, was observed. In 1992, Harriman and Brun reported PET from ethidium and acridine donors to diazapyrenium acceptors under conditions where the redox components were intercalated (Brun, A. M.; Harriman, A. J. Am. Chem. Soc. 1992, 114, 3656). Multi-exponential electron transfer kinetics were attributed to Do-Ac separations of 3, 4, and 5 base pairs. The β value derived in that study (0.88 Å$^{-1}$) is comparable to that determined for Do-Ac systems in proteins, where stacked π-electron systems are not available for mediating electron transfer. Barton, Barbara and co-workers studied transition metal complex donors and acceptors which are intercalated into DNA and found that quenching of the donor fluorescence as well as recovery of the ground state absorption proceeds at rates which are independent of the number of bound acceptors, suggesting a very shallow distance dependence for electron transfer through the DNA duplex (β<0.2 Å$^{-1}$) (Arkin, M. R.; Stemp, E. D. A.; Holmlin, R. E.; Barton, J. K.; Hörmann, A.; Olson, E. J. C.; Barbara, P. F. Science 1996, 273, 475). However, cooperative binding of the donor and acceptor molecules, which would account for the loading-independent kinetics, could not be completely ruled out in that system.

One of the problems associated with the use of non-covalently bound donor and acceptor molecules in these studies is the inability to control precisely the location of the redox components relative to one another when they are bound to the DNA. In one extreme, the intercalation locations will be controlled statistically, leading to a distribution of Do-Ac separation distances. At another extreme, binding will be cooperative, leading to short distances between Do and Ac over a wide range of concentrations.

Covalent linkage of Do and Ac to the 5'-ends of complementary oligonucleotides has led to systems with better defined Do-Ac separation distances. Barton, Turro and co-workers reported fluorescence quenching that occurs in less than one nanosecond for a system containing linked Do and Ac metal complexes intercalated near the ends of a 15 base pair duplex (Murphy, C. J.; Arkin, M. R.; Jenkins, Y.; Ghatlia, N. D.; Bossmann, S.; Turro, N. J.; Barton, J. K. Science 1993, 262, 1025). A rate this fast indicates that the distance dependence of electron transfer through DNA is extremely shallow, but this interpretation must be regarded with caution pending a clear demonstration of redox products. In contrast, there is a report of a covalently linked system having Do and Ac metal complexes at the opposite ends of an 8 base pair duplex which shows electron transfer on a microsecond time scale (Meade, T. J.; Kayyem, J. F. Angew. Chem Int. Ed. Engl. 1995, 34, 352). In this case the redox components were not intercalated within the helix so the rate of electron transfer may simply reflect the time required to orient the donor and acceptor in order to obtain sufficient electronic coupling through the i-electron stack before long distance electron transfer can occur.

At this time, there are many unresolved questions regarding the ability of duplex DNA to mediate electron transfer. None of the systems cited above has unambiguously demonstrated the rate or efficiency of electron transfer between donor and acceptor moieties held at a fixed distance of separation in a DNA/DNA duplex.

In a modification designed to detect hybridization of nucleic acids in homogeneous solution, Tyagi and Kramer (Tyagi, S.; Kramer, F. R. Nature Biotechnology 1996, 14,303) describe a doubly substituted single-stranded DNA construct that possesses a stem-loop (i.e. hairpin) structure. This construct contains a fluorescer covalently linked to one terminus of the strand and an energy transfer quencher of the fluorescer at the opposite terminus. When unconjugated, this single stded chain exists predominantly in a hairpin conformation that constrains the fluorescer and quencher to be relatively close in space. When n this structural form, excitation of the fluorescer with actinic light leads to reduced emission because the fluorescing excited state transfers its energy to the nearby quencher. However, when this single-stranded structure hybridizes with a second strand complementary to its loop region, the distance between the fluorescer and quencher is increased and, consequently, the efficiency of fluorescence increases. The change in fluorescence intensity is an indicator that hybridization has occurred.

The modification described by Tyagi and Kramer offers several advantages for homogeneous real-time assays for hybridization. However there are certain disadvantages to the system they report. First, the indication of hybridization relies on energy transfer quenching of the fluorescer. This requires that the quencher have a lower excited singlet energy than the fluorescer, and his can cause difficulties in selecting a quencher whose absorption spectrum does not overlap with that of the fluorescer. Second, the nature of the hairpin structure requires that a portion of the single-stranded probe molecule be self-complementary. In general, this self-complementary portion will not hybridize with the target strand of the nucleic acid to be determined. This requirement will reduce the association constant of the hybrid duplex DNA. A further disadvantage of the modification described by Tyagi and Kramer is that covalent linkage of the fluorescer and quencher at the terminal positions of the single-stranded DNA probe is cumbersome synthetically and far from ideal for an assay. The long chain of atoms used to bind the fluorescer and donor to the single stranded DNA is flexible and, consequently, the fluorescer and quencher will exist in many conformations, even in the stem-loop structure, some of which may be ineffective at quenching the emission of the fluorescer. This will contribute to a high background fluorescence in assays for hybridization. Finally, a further disadvantage of covalent linkage of the fluorescer and quencher at the terminal positions is that unraveling of the stem structure at these positions, which is commonly to be expected, will increase the distance between the fluorescer and quencher, and increase the number of available conformations. Both of these effects will lead to an increase in background emission.

In a further attempt to modify DNA Shimidzu and co-workers reported the synthesis and characterization of a modified DNA oligomer containing an acridine moiety covaently linked at an internal position (Fukui, K.; Morimoto, M.; Segawa, H.; Tanaka, K.; Shimidzu, T. Bioconjugate Chem. 1996, 7, 349). Hybridization with a complementary oligomer containing either a thymine or an abasic site at the appropriate position opposite the acridine yields a 1:1 duplex with the acridine, apparently, intercalated within the helix. Electron transfer to the acridine moiety was not reported.

Described in WO 95/15971 is the conjugation of oligonucleotides with intercalators that can act as electron donors or electron acceptors. The resulting complexes represent a series of derivatives that are bimolecular templates whose use as probe molecules relies on duplex DNA to provide a path for the transfer of electrons over very large distances at extremely fast rates. In this role the DNA duplex is described as and must function as a "bioconductor". In WO 95/15971 there is disclosure of a method wherein oligonucleotides are labeled at each end with different electron transfer moieties and it is demonstrated that these moieties are capable of electron transfer through the duplex under certain conditions. These electron transfer moieties are complexes of ruthenium and other heavy metal ions with organic ligands which can change electronic state during electron transfer. Further in WO 95/15971, there is a suggestion that the phosphodiester bonds in an oligonucleotide can be replaced by peptide bonds thus using peptide nucleic acids (PNA) as bioconductors.

SUMMARY OF THE INVENTION

The subject of the present invention is a method for determining a nucleic acid in a sample comprising binding a probe having a polymeric backbone different from the natural sugar phosphate backbone of DNA or RNA to the nucleic acid by means of base-mediated hydrogen bonding, wherein this probe has an electron acceptor or an electron donor, or both, bound covalently either at terminal positions or at internal positions of the probe molecule. Further, stimulation of the electron donor or electron acceptor by any one of several means elicits a different outcome depending upon whether the probe molecule is bound to the nucleic acid. In particular, the present invention is a method for inducing an electron or hole transfer from an electron donor to that electron acceptor or a hole transfer from said electron acceptor to an electron donor and determining the occurrence of the electronic transfer as a measure of said nucleic acid. It is an object of the present invention to provide a method for reliable detection of electron or hole transfer.

A further object of the invention is to modify the efficiency or rate of electron (hole) transfer in bioinsulators and bioconductors.

In another aspect, the invention is directed to a method of controlling the rate and efficiency of electron (hole) transfer with high specificity for the indication of duplex formation.

From this prior art it is not apparent to one skilled in the art that DNA/DNA, DNA/PNA and PNA/PNA hybrids will be bioconductors under all conditions of electron transfer driving force and time scale. In particular, electron conduction (electron transfer or hole transfer) from an electronically excited state, or other electron donor or electron acceptor species not having an essentially infinite lifetime, must compete with return of the electronically excited state to its ground state, or consumption by some other means of the electron donor or acceptor with a limited lifetime. If conduction of an electron through a DNA/DNA, DNA/PNA and PNA/PNA duplex occurs on a time scale longer than the return of the excited state to the ground state or consumption of the electron donor or acceptor, then the DNA/DNA, DNA/PNA and PNA/PNA duplex will act as if it is a "bioinsulator", rather than a bioconductor.

The molecular and energetic features that control the rate and efficiency of electron transfer reactions have been extensively studied. The Marcus theory of electron transfer (Marcus, R. A. Ann Rev. Phys. Chem. 1964, 15, 155. Marcus, R. A. J. Chem. Phys. 1965, 43, 679) is remarkably successful in its prediction of reaction rates. In its simplest formulation (eqs. 1 and 2), the theory identifies three factors that determine the rate constant for electron transfer ($k_{et}$). These are the driving force ($\Delta G_{et}$) for the reaction, the reorganization energy ($\lambda$), and the maximum rate constant ($k_{max}$), which occurs when $\Delta G^\neq=0$. In classical theory, $k_{max}=k_{et}\,\upsilon_n$, where $k_{et}$ is the electronic transmission coefficient and $\upsilon_n$ is the frequency of passage through the transition state.

$$k_{et} = k_{\max} \cdot \exp(-\Delta G^{\ddagger} / RT) \quad (1)$$

$$\Delta G^{\ddagger} = \frac{(\Delta G_{et} + \lambda)^2}{4\lambda} \quad (2)$$

Of most relevance to the present invention is the estimation of $k_{et}$ and its comparison with chemical or physical reactions that consume the electronically excited state, or other electron donor or electron acceptor species not having an essentially infinite lifetime. If the rate of electron transfer from donor to acceptor is greater than the rates of the competing chemical or physical reactions, then the electron transfer will be more efficient. Formation of a complex between the probe and the nucleic acid to be determined can change the magnitude of $k_{et}$ and/or the magnitude of the rates of the chemical or physical reactions that consume the electronically excited state, or other electron donor or electron acceptor species not having an essentially infinite lifetime. Formation of the complex between the probe molecule and the nucleic acid to be determined may modify $\Delta G_{et}$ so that the rate of electron transfer increases or decreases upon complex formation. Alternatively, complex formation can cause changes in the environment of the electron donor or electron acceptor such that the rate of chemical or physical reactions that consume the electronically excited state, or other electron donor or electron acceptor species not having an essentially infinite lifetime, changes relative to the rate for the electron transfer reaction. Based on Marcus theory, the formation of the complex between the probe and the nucleic acid to be determined causes a change in the Marcus reorganization energy for the electron transfer or a change in the Marcus $k_{max}$. A change in either parameter may result in either an increase or decrease in the rate of electron transfer. In the case where formation of the complex between the probe and the nucleic acid to be determined results in an increase in the $k_{et}$ the resulting complex can be called a bioconductor, since it facilitates electron transfer. It is a surprising discovery that, depending on some specific details of structure, formation of the complex between the probe and the nucleic acid to be determined results in a decrease in the rate constant for electron transfer in the complex. Thus, in some cases, the complex formed by the probe molecule and the nucleic acid to be determined may be a "bioinsulator".

BRIEF DESCRIPTION OF THE DRAWINGS

FIG. 2 shows a first embodiment of the invention using only one probe molecule labelled with a distally positioned electron donor (Donor) and an internally positioned acceptor (acc.).

FIG. 3 shows an embodiment of the present invention wherein two labelled probes are used. Thus one probe contains the acceptor (distally located) and another probe contains the donor (distally located).

FIG. 6 shows a format using a hairpin forming probe.

FIG. 7 shows an embodiment using two complementary probes.

FIG. 10 shows the flow scheme for the preparation of R1, an electron donating PNA monomer (linker length 4).

FIG. 12 shows absorbance/temperature profiles for PNA/DNA hybrids with different quinone linker lengths for different wavelengths. $AQ_2$ stands for PNA579 and $AQ_5$ stands for PNA586.

DETAILED DESCRIPTION

Figure 1:
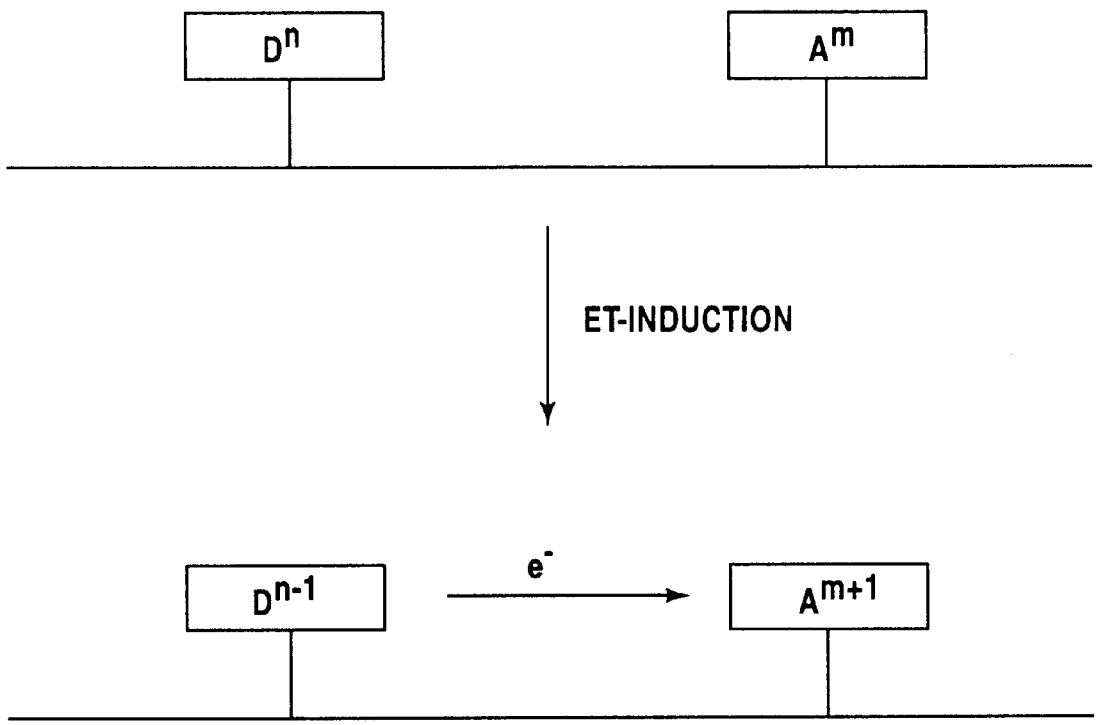
FIG. 1 shows schematically the long range electron transfer (ET) mechanism of the present invention. The concept is illustrated by the example where the donor and acceptor are located on the same strand. The designations n and m refer to the electronic states of the donor and the acceptor.

The term nucleic acid to be determined is understood in the present invention as an analyte nucleic acid or a nucleic acid derived therefrom. Analyte nucleic acids include nucleic acids of any origin, for example, nucleic acids of animal, human, viral, bacterial, or cellular origin. They may be present in solution, suspension, but also fixed to solid bodies or contained in cell-containing media, cell smears, fixed cells, tissues, or fixed organisms. Nucleic acids derived therefrom are nucleic acids prepared from analyte nucleic acids or parts thereof, for example as copies of the above-mentioned nucleic acids, or parts thereof These copies include nucleic acids derived from that original analyte nucleic acids by amplification, including any replication or/and transcription/reverse transcription reactions, for example by the polymerase chain reaction.

Usually the nucleic acid to be determined will be pretreated to get into a condition ready for binding the probe molecule, if it is not already accessible. Such pretreatment may include denaturing double-stranded nucleic acids by changing the pH into the alkaline region, repeating extreme temperature changes (freezing/thawing), changing the physiological probe conditions (osmotic pressure), lysis of cell walls by detergents, chaotropic salts or enzymes (e.g. proteases, lipase). These steps may be used either alone or in combination in order to release the nucleic acids. In some instances, it may be advantageous to separate the nucleic acids from other components of the sample, like proteins, cells, cell fragments, but also nucleic acids which are not intended to be detected.

The probe molecule binding to the nucleic acid is defined by having a polymeric backbone different from the natural sugar phosphate backbone. Examples of such probe molecules are now well-known in the art. Those probes may be based upon monomeric subunits, which are linked in a repetitive way. It is preferable that the probe molecule contains at least five monomeric subunits, each monomeric subunit being connected to other monomeric subunits by peptide bonds. The peptide bond is understood to be the bond connecting a primary or secondary amine and a carboxylic acid residue. Other types of linkages within the monomers or connecting one or more monomers in the backbone are possible, for example, ether or amino bonds. Examples of such probe molecules are described in WO 92/20702 including probe molecules having ligands bound to aza-nitrogen atoms, WO 94/25477, and WO 96/20212. Probe molecules having mixed different linkages between the monomers are described in EP-A-0 672 677. The term probe molecule further contains molecules having the above stretch of the non-natural backbone and an additional stretch of the natural sugar phosphate backbone. Such chimera may possess some lower affinity to complementary nucleic acids, but are nevertheless useful in the present invention.

The term backbone in the present invention shall mean the polymeric moiety to which at different points of attachment heterocyclic base moieties are bound in a consecutive way.

The binding of the probe molecule to the nucleic acid is accomplished by hydrogen bonds mediated by said base moieties on said backbone. Such hydrogen bonding for example occurs between complementary nucleobases as in the base pairing in nucleic acids having the natural sugar phosphate backbone or artificial bases eliciting similar properties for hydrogen bonding to the natural bases. While the most prominent mode of binding is by duplex formation, some molecules bind to nucleic acids by triplex formation (see for example WO 95/01370). Artificial bases include diaminopurine, pseudouridine, thioguanine and 7-deazaguanine. The method of the invention requires a stretch of at least five consecutive monomeric units coupling the bases of the probe molecule. The probe molecule should have a length of at least 9 base-pairing monomeric units, preferably between 9 and 30 and most preferably between 10 and 25 base-pairing monomeric units.

Such probe molecules can be prepared by analogy to the methods described in the above-mentioned documents. Their preparation may include techniques usually employed in peptide chemistry. However, probe molecules especially preferred in the present method include new starting and intermediate compounds useful for introducing any electron donor or/and any electron acceptor moieties into the probe. Their preparation will be described later.

An electron acceptor or an electron donor or an electron acceptor and an electron donor are bound covalently to the probe molecule at defined, fixed positions, according to the invention. The generally possible positions for attaching moieties to polymeric backbones can be systematically divided into a first group wherein the moiety is attached at one or both ends of the polymeric backbone, a second group wherein at least one of the groups is bound to the polymeric backbone at a position on the backbone not located on the first and the last base bearing monomeric unit of said backbone, and a third group wherein the moiety is bound to a base position attached at any of the monomeric units. Surprisingly, the objects of the present invention are better met for the second group. Within this group, such probe molecules have proven to be the most successful in which the nucleobase moiety of one or more of the monomeric subunits is replaced totally by a group or groups containing the electron acceptor or an electron donor, preferably such that the rate or efficiency of electron transfer in the probe is modified by the nucleobases of the nucleic acid to be determined. It is possible not only to modify only one subunit by such moieties, but also more subunits, dependent upon the overall length of the probe molecule. However, as a general rule, it is preferred to not include more than 30% of modified monomeric units compared to the overall number of monomeric units in the probe molecule. If more than one modified monomeric subunit is contained within the probe molecule, these monomeric units should not all be located at the final monomeric subunits.

Preferred probe molecules are compounds of the general formula I

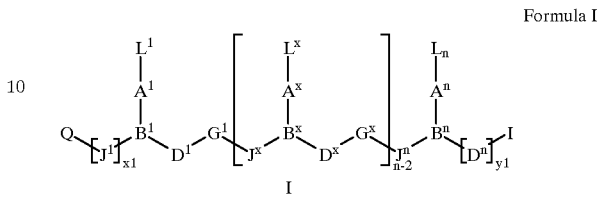

Formula I wherein n is an integer of from at least 3, x is an integer of from 2 to n−1, each of $L^1$–$L^n$ is a ligand independently selected from the group consisting of hydrogen, hydroxy, ($C_1$–$C_4$)alkanoyl, naturally occurring nucleobases, non-naturally occurring nucleobases, aromatic moieties, DNA intercalators, nucleobase-binding groups, heterocyclic moieties, reporter ligands and chelating moieties, wherein at least one of $L^1$–$L^n$, preferably at least one of $L^2$–$L^{n-1}$ is a non-nucleobase electron acceptor or a donor moiety and at least 2 of $L^1$–$L^n$ being a nucleobase binding group, or a naturally or non-naturally occurring nucleobase;

each of $J^1$–$J^n$ is $(CR^6R^7)y$ (preferably $CR^6R^7$, $CHR^6CHR^7$ or $CR^6R^7CH_2$) where $R^6$ is hydrogen and $R^7$ is selected from the group consisting of the side chains of naturally occurring alpha amino acids, or $R^6$ and $R^7$ are independently selected from the group consisting of hydrogen, ($C_1$–$C_6$)alkyl, aryl, aralkyl, heteroaryl, hydroxy, ($C_1$–$C_6$)alkoxy, ($C_1$–$C_6$)alkylthio, $NR^3R^4$ and $SR^5$, where $R^3$ and $R^4$ are as defined below, and $R^5$ is hydrogen, ($C_1$–$C_6$)alkyl, hydroxy, ($C_1$–$C_6$)alkoxy, or ($C_1$–$C_6$) alkylthio-substituted ($C_1$–$C_6$)alkyl or $R^6$ and $R^7$ taken together complete an alicyclic or heterocyclic system; or $C^1$–$C^n$ is CO, CS, $CNR^3$;

each of $D^1$–$D^n$ is $(CR^6R^7)_z$ (preferably $CR^6R^7$, $CHR^6CHR^7$ or $CH_2CR^6R^7$) where $R^6$ and $R^7$ are as defined above;

each of y and z is zero or an integer from 1 to 10, the sum y+z being at least 2, preferably greater than 2, but not more than 10;

each of $G^1$–$G^{n-1}$ is —$NR^3CO$—, —$NR^3CS$—, —$NR^3SO$— or —$NR^3SO_2$—, in either orientation, where $R^3$ is as defined below;

each of $A^1$–$A^n$ and $B^1$–$B^n$ are selected such that:

(a) $A^1$–$A^n$ is a group of formula (I/A), (I/B), (I/C) or (I/D), and $B^1$–$B^n$ is N or $R^3N^+$; or (b) $A^1$–$A^n$ is a group of formula (I/D) and $B^1$–$B^n$ is CH;

Formula I/A

Formula I/B

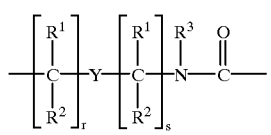

Formula I/C

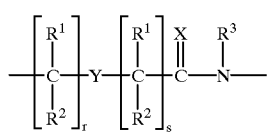

Formula I/D wherein:

X is O, S, Se, $NR^3$, $CH_2$ or $C(CH_3)_2$;

Y is a single bond, O, S or $NR_4$;

each of p and q is zero or an integer from 1 to 5, (the sum p+q being preferably not more than 5);

each of r and s is zero or an integer from 1 to 5, (the sum r+s being preferably not more than 5);

each $R^1$ and $R^2$ is independently selected from the group consisting of hydrogen, $(C_1-C_4)$alkyl which may be hydroxy- or $(C_1-C_4)$alkoxy- or $(C_1-C_4)$alkylthio-substituted, hydroxy, $(C_1-C_4)$alkoxy, $(C_1-C_4)$alkylthio, amino and halogen; and each $R^3$ and $R^4$ is independently selected from the group consisting of hydrogen, $(C^1-C_4)$alkyl, hydroxy- or alkoxy- or alkylthio-substituted $(C_1-C_4)$alkyl, hydroxy, $(C_1-C_6)$-alkoxy, $(C_1-C_6)$-alkylthio and amino;

Q and I is independently selected from —$CO_2H$, —CONR'R", —$SO_3H$ or —$SO_2$—NR'R" or an activated derivative of —$CO_2H$ or —$SO_3H$ and —NR'R''' where R', R" and R''' are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, including both oligoribo-nucleotides and oligodeoxyribo-nucleotides, oligonucleo-sides and soluble and non-soluble polymers and as well as nucleic acid binding moieties and each of x1 and y1 is an integer of from 0 to 10.

Alkoxy- and alkylthio groups contain preferably from 1 to 4 carbon atoms.

An example for a fused aromatic moiety is naphthol. A heterocyclic moiety is pyridin. Reporter groups are moieties that can be detected, like fluorescent compounds, for example fluorescein, or moieties that can be recognized by another molecular entity, like haptens which can be recognized by an antibody raised against this hapten.

In the above structures wherein Q or I is an oligonucle-otide or oligonucleoside, such structures can be considered chimeric structures between PNA compounds and the oli-gonucleotide or oligonucleoside.

Linkers $A^1$–$A^n$ for binding acceptor moieties are gener-ally preferred at a length of between 1 to 10 atoms, most preferred 2 to 6 atoms, for donor moieties at a length of 1 to 10, most preferred 2 to 8 atoms.

More preferable are compounds of subgroups Ia–Ib based on the general formula I wherein (Ia): $B^1$–$B^n$ is N and $A^1$–$A^n$ is —CO—$(CH_2)_6$—

(Ib): $B^1$–$B^n$ is N and $A^1$–$A^n$ is —CO—$NR^3$—$(CH_2)_2$—

(Ic): $B^1$–$B^n$ is CH and $A^1$–$A^n$ is —$N^3$—CO—$(CH_2)_2$—

Preferred PNA-containing compounds useful to effect binding to RNA, ssDNA and dsDNA and to form triplexing structures are compounds of the formula IIa, IIb and IIc:

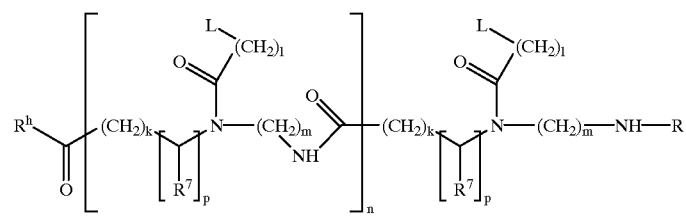

Formula IIa

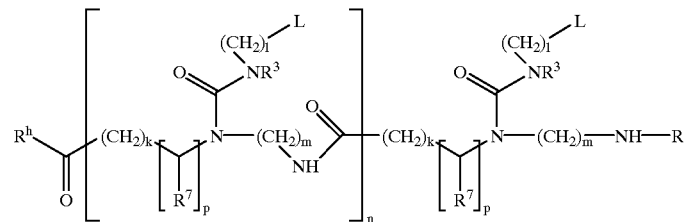

Formula IIb

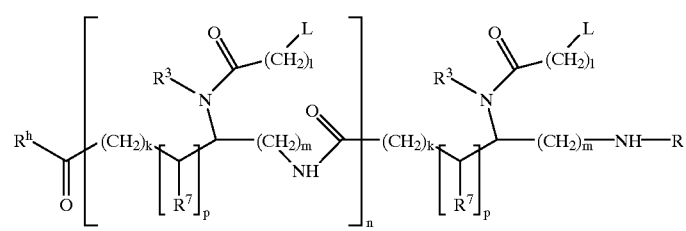

Formula IIc wherein:

each L is independently selected from the definitions of $L^1-L^n$ in formula I;

each $R^7$ is independently selected from the group consisting of hydrogen and the side chains of naturally occurring alpha amino acids;

n is an integer greater than 1, each k, l, and m is, independently, zero or an integer from 1 to 5;

each p is zero or 1;

$R^h$ and $R^i$ are as defined for R', R" and R'"

Electron acceptor moieties and electron donor moieties are each referred to as electron transfer moieties. They are most preferably moieties not including nucleobases (non nucleobase moieties).

Electron acceptors according to the present invention can induce oxidation of other moieties by attracting an electron from their surroundings particularly after they have been stimulated with light or activated by some other means. Electron acceptors will typically be electron-deficient species. Preferable electron acceptors are organic molecules, preferably excluding organic molecules containing metal ions. Further, these organic molecules have a generally flat structure with a system of delocalized π-electrons. Therefore, organic molecules are especially preferred that contain aromatic hydrocarbon moieties containing functional groups, wherein the functional groups may have electron-withdrawing properties. It is possible that the electron acceptor will contain both electron-donating and electron-withdrawing functional groups. The substituents should not be so bulky that they disturb the regular base stacking between the probe and the nucleic acid to be determined. The electron deficiency of the electron acceptor will normally be increased by excitation with light or with stimulation by some other means. In the preferred case there is no measurable electron transfer to the acceptor without its stimulation in the assay medium. The acceptor moiety will typically have well-characterized redox and spectroscopic properties, although precise knowledge of these parameters is not required for their successful application in this invention. Electron acceptors useful in this invention typically undergo a change in chemical or optical properties when it accepts an electron. For example, such electron acceptors may be useful in this invention when, after conversion by electron attraction to become a radical anion, or any other one electron reduction product, it possesses a unique optical spectrum with strong absorption bands. However, the detection of the change in chemical or optical properties of the electron acceptor is not required for the successful application of this invention.

These acceptor moieties are typically composed of one to 10, preferably 1 to 4, fused cyclic hydrocarbon rings which may be substituted or unsubstituted. The cyclic hydrocarbons may independently have any ring size ranging from 5- to 10-membered rings, but preferably include 5- or 6-membered aromatic rings. The cyclic hydrocarbons may be fused in any position isomer.

Preferably, the acceptor or the donor moiety includes a group of general formula IIIa or IIIb

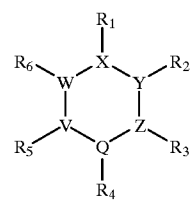

IIIa

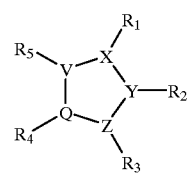

IIIb wherein X, Y, Z, Q, V and W are independently selected from the atoms C, N, S, and O, X, Y, Z, Q, V and W are connected by either single or double bonds. $R_1-R_6$ are independently selected from the group of $R_1-R_6$ are, independently from each other, selected from the group of —H, —O⁻, —OH, —OR', —SH, —SR', —NH$_2$, NO$_2$, —SO$_3^-$, —SO$_2^-$, —CN, —PO$_3^{2-}$, —PO$_2^-$—, ——COOH, —CO—R', —COOR', —CS—R', CSO—R', —COO⁻, —N═N—, halogen (—F, —Cl, —Br, —I), —NHR', N(R'R"), or derivatives hereof, or hydrocarbyls or heterocyclyl as defined below. R' and R" is chosen from the possible definitions of $R_1-R_6$. At least one of X, Y, Z, Q, V and W can together with the moiety $R^1-R^6$ bound thereto also mean —CO—, —SO— or —SO$_2$—. At least one of $R^1-R^6$ can also be a single or a double bond.

Hydrocarbyl comprises groups such as alkyl, alkenyl, alkynyl, each having between 1 and 10 carbon (C)-atoms, aryl having 6–30 C-atoms, such as phenyl, naphthyl, biphenyl, tolyl, anthracenyl, etc., and combinations of these in different substitutions patterns. These hydrocarbyl groups may be straight chained or branched chained, symmetric or asymmetric, chiral or achiral, contain one or more hetero atoms selected among —N—, —NH—, —S—, —O—, and may also be fused. The hydrocarbyl groups may be unsubstituted or substituted by one or more of the above mentioned $R^1-R^6$.

Heterocyclyl are preferentially selected among cyclic aromatic or non-aromatic moieties containing hetero atoms selected among —N—, —NH—, —S— and —O—, preferably selected from the group consisting of pyridyl, imidazolyl, pyrimidinyl, pyradazinolyl, quinolyl, acridinolyl, pyrrolyl, furyl, thienyl, isoxazolyl, oxazolyl and thiazolyl. The heterocyclyl groups may optionally be substituted by one or more of the above mentioned $R^1-R^6$.

At least one of said moieties $R^1-R^6$ is modified such that it is capable of binding to the backbone of the probe. Preferably the electron acceptor is bound via a free sigma bond at one of said moieties to said backbone. It is understood according to the present invention that the acceptor moiety is defined as the moiety which is capable and responsible for accepting the electron. Any moiety between the backbone and the acceptor is defined to be a linker A.

While this is not the preferred case, the acceptor or/and donor moiety can include a complex of a transition metal chelated by one or more ligand moieties. Preferred transition metals are chosen from the group iron, copper, ruthenium, rhenium and osmium.

More preferably, the electron acceptor or donor may contain a group chosen from the class of imides. Imides may act as both acceptors and donors. These compounds will contain the essential —(C=O)—N(R)—(C=O)— unit with the carbonyls placed in a hydrocarbon ring structure which is bonded to an aromatic ring system via conjugation of the carbonyls. The imide is contained in a hydrocarbon ring which may be 5, 6, 7, 9 membered but preferentially a 5 or 6 membered ring. The acceptor/donor may contain from 1–10 imides linked via the aromatic system. An acceptor/donor may contain imides of the same ring size or containing imides of different ring sizes. The aromatic structure comprises of 1–10 fused cyclic aromatic hydrocarbons and optionally substituted with the substituents (R). The cyclic hydrocarbons may be bonded/fused in any position isomer. The cyclic hydrocarbons may independently of each other be any ring size (5, 6, 10, 14 membered rings) but preferentially 5, 6 membered aromatic rings which independently of each other may comprise one or several hetero atoms selected among —N—, —NH, —S— and —O—. Preferred imides include groups of general formulae IVa–IVe.

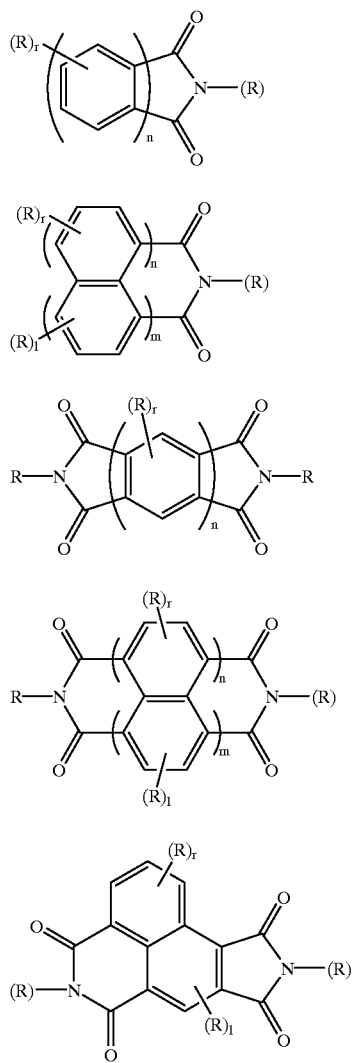

wherein the definitions for R are selected from the possible definitions of $R^1$–$R^6$ of general formula IIIa and IIIb and wherein n and m is 0 or an integer from 1 to 10 and k, r and l is 0 or an integer from 1 to 4. It is clear that only so many substituents R are bound that the valency and charge of the atom of attachment of the substituent R is not changed.

A further preferred moiety is chosen from the group of n-alkyl-aza-aromatic compounds. N-alky-aza-aromatics may act as both acceptors and donors (formula Va–d, vide infra). In these compounds the nitrogen atoms in the aromatic rings are alkylated. This forms positively charged molecules. The aromatic rings where the aza atoms are located can be 5, 6, 10, 14 membered rings, but preferentially 5 and 6 membered rings. The acceptor/donor may contain 1 to 10 alkylated cyclic nitrogen atoms which are placed in an aromatic system of 1 to 10 fused aromatic rings.

The fused cyclic hydrocarbon system may be composed of 5, 6, 10, 14 membered aromatic rings, but preferentially 5 and 6 membered rings, which independently of each other may comprise one or several hetero atoms selected among —N—, —N, —S— and —O—. The acceptor may be composed of alkylated cyclic nitrogen atoms of the same ring size and/or different ring size. The aromatic hydrocarbons carrying the alkylated cyclic nitrogen atoms and/or the fused aromatic ring not carrying the alkylated nitrogen atoms are preferentially substituted (R).

Within this group compounds of general formulae Va–Vd

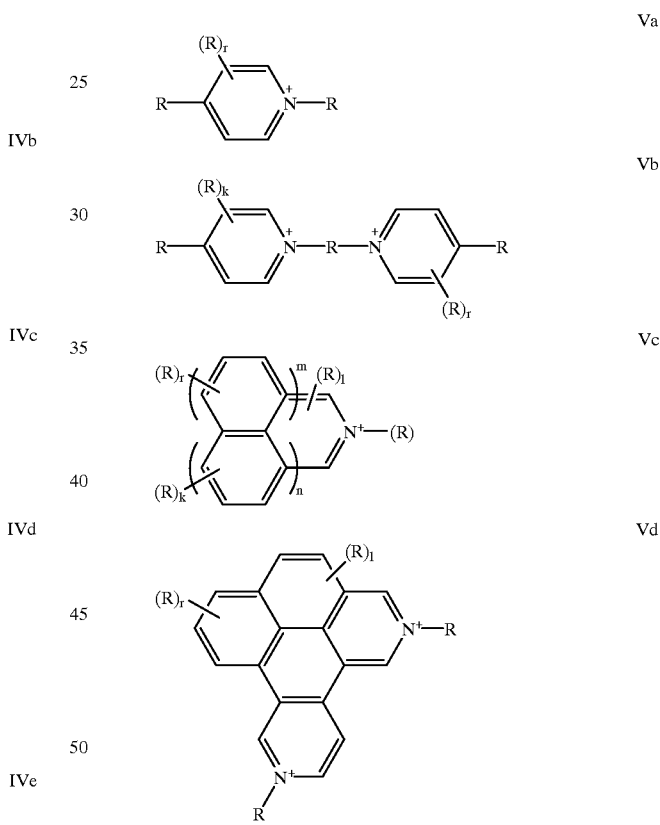

wherein the definitions of the substituents of formula IV apply and wherein r is 0 or an integer of from 1 to 4.

Preferred as acceptors are compounds containing a quinoid structure. Such compounds are well-known to one skilled in the art. The quinones especially useful in this invention are composed of at least 2 conjugated carbonyl groups (optionally thiono or azo) placed in the same or in separate rings fused with 1–10 cyclic aromatic hydrocarbons and optionally substituted with the substituents ($R^1$–$R^6$) and having 2–20 conjugated carbonyl groups in pairs, provided that the number of conjugated carbonyl groups does not exceed twice the number of fused cyclic hydrocarbons. The cyclic hydrocarbons may be fused in any position isomer.

The cyclic hydrocarbons may independently of each other be any ring size but preferentially 5, 6 carbon atom membered aromatic rings which independently of each other may comprise one or several hetero atoms selected among —N═, —NH, —S— and —O—. The conjugated carbonyl groups may be located in any of these rings provided that the quinoid structure is maintained.

Especially preferred quinoid structures contain the general formulae VIa–VIc.

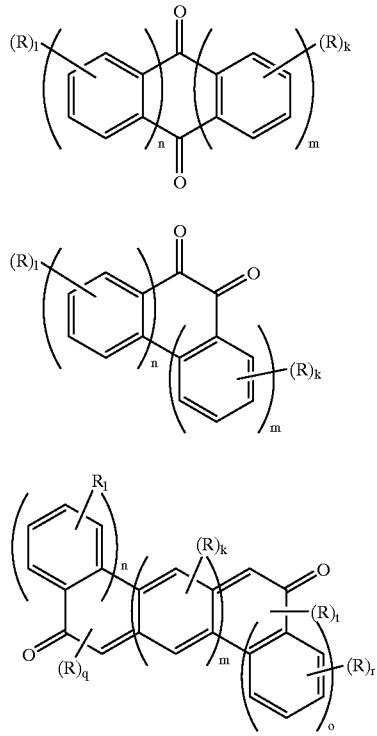

wherein the definitions of the substituents are chosen from the definitions of formulae IV and wherein o and p are 0 or an integer from 1 to 10 and t and q are 0 or an integer from 1 to 4. Preferred examples of this group are anthraquinone and phenanthraquinone.

As electron donors, generally all compounds are useful which can in the ground state or in the electronically excited state, or after stimulation by some other means, be oxidized by an electron acceptor by giving off an electron. Preferred donors are organic molecules, although organic molecules containing metal ions are not excluded. Preferably, the donor molecules are chosen such that the electron deficiency caused by the oxidation has the consequence of causing a change to one or more of its physical or chemical properties, whereby detection of the electron deficiency (oxidation event) is possible. Typical donors will be electron-rich fused aromatic systems carrying functional groups and will optimally be substituted. The donor will preferably have an aromatic structure substituted by electron-donating groups. Therefore, the donors are preferably chosen from the general formulae III–V, wherein the substitution with electron-donating groups supersedes.

Electron-withdrawing groups or electron-attracting groups are preferably the groups $NO_2$, $-SO_3^-$, $-SO_2^-$, $-CN$, $-PO_3^{2-}$, $-PO_2^-$, $-COOH$, $-CO-R'$, $-COOR'$, $-CS-R'$, $CSO-R'$, $-COO^-$, halogen ($-F$, $-Cl$, $-Br$, $-I$), while electron-releasing groups/electron-donating groups are preferably selected from the groups H, $-O^-$, $-OH$, $-OR'$, $-SH$, $-SR'$, $-NH_2$, $-N=N-$, $-I$, $-NHR'$, $N(R'R'')$.

Compounds preferentially acting as donors are compounds containing an aza-aromatic structure. Examples of these compounds are aromatic ring structures containing nitrogen The N-heterocyclic structure is bonded/fused with a cyclic hydrocarbon system composed of 5, 6, 10, 14 membered aromatic rings, but preferentially 5 and 6 membered rings, which independently of each other may comprise one or several hetero atoms selected among —N═, —NH, —S— and —O—. The donor may be composed of heterocyclic nitrogen containing rings of the same ring size and/or different ring size. The aromatic hydrocarbons carrying the heterocyclic structure and/or the bonded/fused aromatic ring system are preferentially substituted.

Preferred aza-aromatic structures are compounds of general formulae VIIa–VIIc

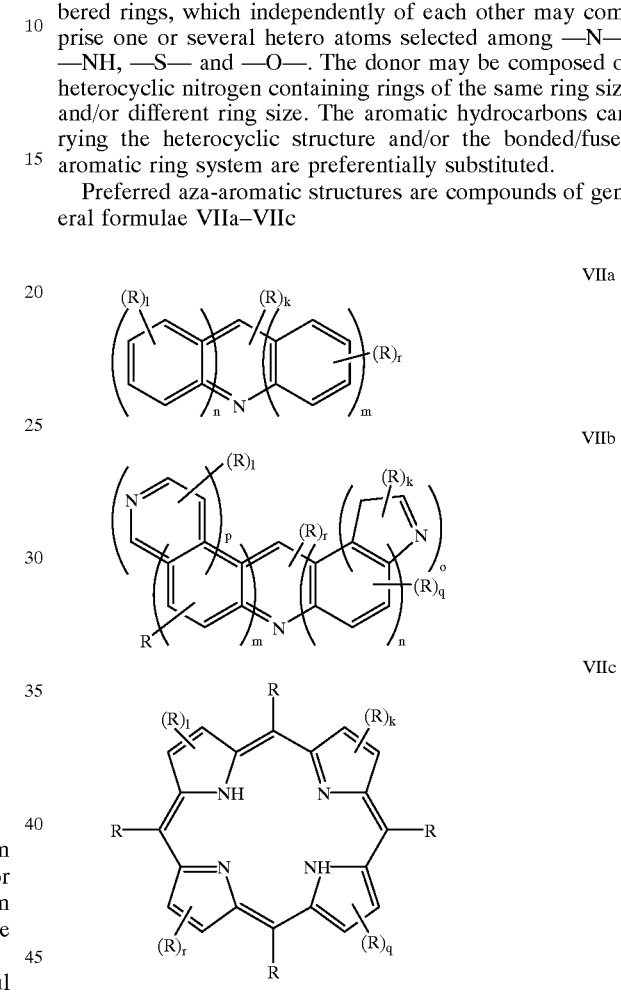

wherein the groups R, n, m, p, o, l, k, q, and r are chosen from the definition of formulae III to VI.

One possible donor moiety is the natural base guanine and derivatives thereof. It has been found in the present invention that guanine is an effective donor, forming a chemically reactive species.

FIG. 1 shows schematically one embodiment of the present invention. The probe strand contains a donor moiety D having n electrons and an electron acceptor A having m electrons covalently attached. Upon induction of electron transfer (ET) one electron is transferred from the donor moiety to the acceptor moiety, thereby changing the number of electrons in each moiety.

While applicants do not wish to be bound on this hypothesis, it appears that the use of nucleic acid analogues allows very selective control of the rate or efficiency of electron and hole transfer between a donor and an acceptor through modification of the distance or effectiveness of electron or hole transport through the -electron stack of the DNA or the nucleic acid analogue when bound to a complementary nucleic acid strand. The orientation within such a complex is considered to be so rigid that the donor (acceptor) after excitation, or stimulation by some means, can donate (attract) an electron (hole) from a near-by acceptor (donor) or a nucleic acid base. The base where the electron or hole comes from is now oxidized or reduced and may bear a positive or negative charge. The acceptor as a consequence is negatively charged. When a chemical moiety (here a nucleobase) is missing an electron, an "electron hole" (or just hole) is created in the molecule. The electron hole in the first base can then be filled by transfer of an electron from another base (see FIG. 5); this process is called hole-hopping. By several such hole-hops, the excitation of the acceptor and subsequent electron transfers yield oxidation of a distal position in the binding product (for example, a hybrid between the nucleic acid analogue and the nucleic acid to be determined). Electron transfer may propagate in the strand where it is initiated but may as well propagate in the opposite strand. The rate or efficiency of electron or hole hopping will depend on its time scale and the time scale of chemical or physical processes that compete for consumption of the excited or stimulated electron donor or acceptor.

Figure 5:
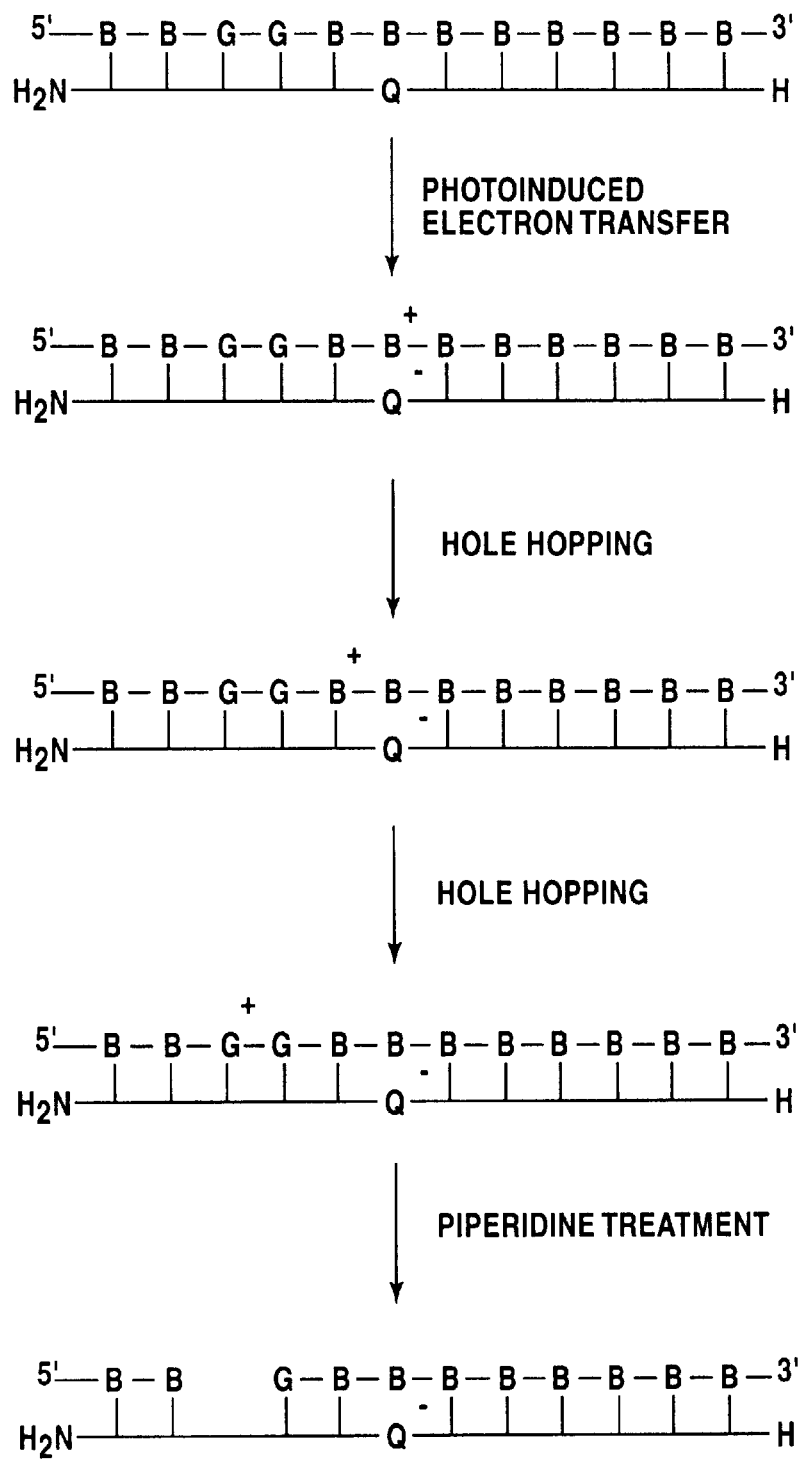
FIG. 5 shows the proposed electron transfer mechanism via hole hopping.

FIG. 5 shows schematically the process of hole-hopping initiated by irradiation at 350 nm for a peptide nucleic acid (lower strand) having an electron acceptor exemplified as Q within the sequence and replacing a base and a nucleic acid (upper strand) having bases B complementary to the bases of the peptide nucleic acid. Electron transfer creates a positively charged base at the nucleic acid ($B^+$) by hole-hopping. This positive charge is preferentially transmitted to the 5'-terminal base of a GG sequence, eventually causing chemical damage to this base. Upon treatment with piperidine, the linkage between the damaged base and the nucleic acid backbone is cleaved. Release of the base then permits scission of the analyte backbone, resulting in formation of smaller fragment molecules which can be readily detected by electrophoretic or chromatographic techniques. One aspect of the present invention is to use this electron transfer from an electron donor on the analyte to an electron acceptor covalently linked to the probe molecule and subsequent cleavage of the analyte to detect hybridization. The present invention is further based on the fact that this electron transfer is possible only if this complex between the nucleic acid to be determined and the nucleic acid analogue is formed, since single-stranded PNA probes react with analyte nucleic acids by electron transfer either not at all or at a much lower rate if the two strands are not hybridized. The rate or efficiency of electron transfer is significantly reduced for complexes having an internal mismatch. In this aspect of the current invention it is preferable that the electron transfer not be reversible.

The sample containing the nucleic acid to be determined is contacted with the probe molecule in order to create the complex between that probe molecule and the nucleic acid to be determined. This complex will form via base-mediated hydrogen bonding. Peptide nucleic acids as probe molecules have the advantage that they can strand invade into double-stranded nucleic acids. Therefore, it is not even necessary to separate double-stranded nucleic acids into single strands prior to adding the probe molecule. The binding of the probe molecule to the nucleic acid will be made according to conditions known to one skilled in the art. Such conditions are well described for peptide nucleic acids, for example in WO 92/20703, to which is made reference in this respect. Because in many cases, the amount of nucleic acids in the sample is not evident, it might be preferred to choose the probe molecule in the amount exceeding the highest expected amount of nucleic acids in the sample. However, in order to maintain a low level of background signal, it may be advisable to choose the amount of probe molecules to be in the order of magnitude of the nucleic acid to be expected. As described in WO 95/15971, there are several possibilities to determine the presence of any nucleic acid. The present invention, however, requires that at least one probe molecule is labelled by an electron donor moiety or an electron acceptor moiety or both. The ruling principle is that within the complex containing the nucleic acid to be determined and the probe molecule, there is at least one electron donor and at least one electron acceptor moiety. While one of the electron donor and electron acceptor moiety must be covalently bound to the probe molecule, at least one of the other species of electron transfer moieties can be located either within the same probe molecule, the nucleic acid to be determined or another probe molecule. This other probe molecule can either have a natural sugar phosphate backbone or a non-natural nucleic acid analogue backbone, while the nucleic acid to be determined preferably has the natural sugar phosphate backbone.

In a first embodiment, a complex is formed by a nucleic acid analogue probe molecule having an electron acceptor moiety bound at an internal backbone position, the nucleic acid to be determined or a nucleic acid being the product of an amplification process of a nucleic acid to be determined, and a further probe nucleic acid analogue probe molecule containing an electron donor moiety bound to the backbone at a non-terminal position, wherein the probe molecules are bound to different but adjacently located nucleotide sequences on the nucleic acid. It is important to avoid interrupting the base-stacking between the binding sites of the two probes. As a general rule, the electron donor and the electron acceptor of two different probe molecules should not be at termini facing each other when bound to the nucleic acid. It is obvious that groups at the termini facing each other would severely hinder the capability of the probes to bind to adjacent sequences on the nucleic acid to be determined.

In a second embodiment, the nucleic acid is labelled to contain an electron donor or electron acceptor moiety within the π stack. As described for the probe molecule, it is therefore preferred to insert a flat electron transfer moiety in place of a nucleobase. Such nucleic acids can for example be prepared by using a chemically synthesised oligonucleotide primer having the electron transfer moiety near the 3'-end. During amplification, if the original analyte nucleic acid is present, this primer is elongated by attachment of further mononucleotides. The probe molecule is then chosen to bind to a position containing both the part of the primer wherein the electron transfer moiety is located and a part of the adjacent extension product.

For the further determination of the complex, it is important that by this binding process a complex is formed having at least one electron acceptor moiety and at least one electron donor moiety covalently bound to either of the probe molecules or the nucleic acid to be determined. Thus, the complex contains at least one electron acceptor and at least one electron donor.

The formation of the complex is determined by inducing electron transfer from an electron donor within that said complex to an electron acceptor within said complex and determining the occurrence of this electronic transfer as a measure of said nucleic acid. This induction of electronic transfer of course depends upon the choice of the electron donor or/and the electron acceptor. There are at least two possibilities to start induction. In the first case, the electron donor is activated to give away an electron to the π-stack within the complex. In the second case, the electron acceptor is activated to absorb an electron from a moiety within the π-stack as described above. Generally, therefore the electron acceptor is changed in its electronic configuration, which will depend upon the π-systems involved. The activation process is described in the following using the example of compounds chosen from the general formula V. For example, anthraquinone derivatives have an nπ* excited state electronic configuration. Upon excitation by light, fast (≦10 ps) intersystem crossing to the triplet state will occur, precluding fluorescence emission. However, phosphorescence from the triplet state can be observed at low temperatures. This emission is efficiently quenched when the electron acceptor is intercalated into the π-stack of the complex formed due to rapid electron transfer from one of the bases adjacent to the intercalation site to the excited electron acceptor. When the electron acceptor is not located within the π-stack, electronic interaction with the bases is weak at best and significantly reduced quenching occurs.

In a first embodiment therefore the occurrence of electronic transfer is determined by determining the degree of the reduction of quenching compared to the case when no nucleic acid to be determined is present.

The preferred mode of inducing electron transfer in this aspect of the invention is therefore the inducement by irradiating the sample containing the complex with light at a wavelength wherein the activation of the electron acceptor is achieved. This will be for the electron acceptors mentioned above at wavelength of between 300 nm and 450 nm, most preferably between 330 nm and 360 nm. The vessel or containment wherein the sample is maintained preferably is transparent to the light used, such that the light yield is improved.

The generation of electron transfer (ET) is preferably done in an aqueous environment. Thus, the solvent used is preferentially water or water containing up to 40% (v/v) of an organic medium, preferentially up to 10% (v/v) of an organic solvent such as methanol. Higher content of organic solvents will not be used due to the instability of duplexes formed from nucleic acids and nucleic acid analogues, such as PNA, under these conditions.

The solvent will preferentially be buffered and the pH range will be 2–12. Buffers can be selected among the traditionally used buffers in biological assays, but will often be phosphate buffers at pH 7. The salt concentration in the buffer may vary but will preferentially be in the range of between 10 mM and 0.5 M.

It may be advantageous to mix the reaction mixture containing the complex during irradiation, such that homogeneous inducement is achieved.

Further possible ways for inducing electron transfer include stimulation of the electron acceptor at an electrode or by chemical means, or by irradiation with electrons, or by subjecting the samples to ionising electromagnetic radiation.

The time in which the stimulation conditions are maintained depends upon the strength of stimulus. It is apparent to one skilled in the art that if a strong stimulation source is used, inducement may be accomplished in a shorter time than when using a low strength source. In order to keep the time for the assay limited it is preferred to have irradiation times of less than 6 hours, more preferably less than 1 hour. A practical lower limit for the stimulation time may be less than 1 second. At high stimulation power there is a chance that damage to either the sample or the sample's environment will occur.

The electron transfer induced is determined as a measure of the nucleic acid to be determined. The occurrence of the electron transfer can be measured by several methods. They may include determining the electron transfer itself or may comprise the determination of any changes occurring within the complex or its components caused by the electron transfer. It is especially preferred to determine the changes within the electron acceptor either immediately after the electron transfer or at some time later when the process has reached its final state. The most obvious change of the electron acceptor is the absorption of the electron, changing the electronic configuration of the electron acceptor or donor. This change can be measured using either chemical or spectroscopic properties of the now electron-rich electron acceptor. Most preferred are determinations of the spectroscopic properties, such as light absorption or emission at characteristic wavelengths (or quenching thereof). The electron-rich electron acceptor may also be determined by chemical or physical means such as transferring its excess electron to a secondary acceptor or an electrode.

The electron donor has also changed its chemical and spectroscopic characteristics by losing an electron. For example, if guanine is the electron donor, by losing an electron a reactive species is created which renders the nucleic acid backbone susceptible to cleavage specifically at the site of oxidation by piperidine treatment. This chemical reaction is known to one skilled in the art. The occurrence of electronic transfer can then be determined by detecting nucleic acids or probe molecules being shorter in length than expected. This can be made either by direct gel-electrophoresis or after sequencing as well as by liquid chromatography methods.

In case of electron donors changing their spectroscopic characteristics upon losing an electron, the spectroscopic characteristics of the modified electron donor can be determined. Similar to the determination of any changes in the acceptor, it is possible to spectroscopically determine the presence of the created species using its light absorption or fluorescence at characteristic wavelength.

A further indication of the electron transfer is quenching of a possible luminescence of the electron donor or electron acceptor. It is well known to those skilled in the art that electronically excited states of many electron donors or electron acceptors emit light. Electron transfer reactions can effectively quench this emission. In one aspect of this invention, quenching of the luminescence of the excited electron donor or the excited electron acceptor is the means by which formation of the complex between the probe and the nucleic acid is determined. For example, luminescence from the electron donor or electron acceptor will be reduced by formation of the complex if the rate or efficiency of electron transfer is increased by complex formation. In the preferred application of this invention, the luminescence from the excited donor or acceptor is increased by complex formation because the rate or efficiency of electron transfer has decreased as a consequence of complex formation.

In addition to the dependence of the reaction rate on the free energy, reaction rate will also be dependent on distance. In particular, the reaction rate is expected to decrease exponentially with distance:
where r is the distance separating the donor and acceptor and $\beta$ is a dampening factor with units of distance$^{-1}$. The dampening factor $\beta'$ a measure of the conductivity of the medium: a low $\beta$ will allow electron transfer to occur over very long distances while a high $\beta$ will permit electron transfer at short distances only.

There is currently some controversy regarding the $\beta$ value for duplex DNA: Barton and coworkers have suggested that $\beta$ could be very low (<0.2 Å$^{-1}$) (Murphy, C. J.; Arkin, M. R;

Jenkins, Y.; Ghatlia, N. D.; Bossmann, S. H.; Turro, N. J.; Barton, J. K.; Science 1995, 262, 1025–1029), while Harriman and Brun have measured a β value of 0.88 Å$^{-1}$ (run, A. M.; Harriman, A. J. Am. Chem. Soc. 1992, 114, 3656–3660). The Barton value would suggest that duplex DNA is an exceptional conductor while the Harriman/Brun value would suggest that duplex DNA is an ordinary conductor. The Barton value is not well-substantiated by experiment (i.e. the occurrence of electron transfer has not been demonstrated) so the Harriman/Brun value seems more reliable at this time. It should also be noted that the β values for PNA-DNA and DNA-DNA could be quite different since the electron which is transferred is passing through the π-stack and the structures of the π-stacks are quite different for the two types of duplexes.

If one assumes a "normal" β value of ca. 1.0 Å$^{-1}$, then a change in distance from 10 to 20 Å would decrease the electron transfer rate by more than four orders of magnitude. Such a strong dependence of the electron transfer rate on distance is the foundation of our distinction between bioconductors and bioinsulators, particularly with respect to the severe time constraints imposed on the system by using photoinduction. The excited state species used as either the donor or acceptor will exist for a relatively short time. In a preferred embodiment, the donor absorbs photon and has a relatively short lifetime, meaning it will relax to the ground state within a few nanoseconds of excitation. This relaxation can occur by several mechanisms but the most important pathway is fluorescense, in which photon of light is emitted. In the presence of a suitable electron acceptor, resulting in a decrease in the fluorescence. "Suitability" is determined by the acceptor reduction potential: ideally, the potential will be sufficiently low to yield a negative free energy for electron transfer. If the potential is too high, then the electron transfer will be too slow to compete effectively with fluorescence and little quenching will result. Therefore, the strong dependence of electron transfer rates on distance indicate that, with the proper donor/acceptor pair, one can convert a system from a bioconductor to a bioinsulator simply by increasing the donor-acceptor separation distance. The key is to increase the distance (decrease the reaction rate) until the electron transfer becomes too slow to compete with fluorescence.

In the PNA hairpin system we take advantage of the large increase in distance separating the donor and acceptor after hybridization in order to inhibit electron transfer. The fact that we observed significantly more fluorescence after hybridization than in the hairpin conformation indicates that β is not very small. However, the lack of complete quenching in the hairpin (i.e. a non-black background) arises because the free energy for electron transfer is not optimum for the acridine/quinone pair, so even in the folded conformation, the fluorescence and electron transfer are competing. Two things can be done to improve the system: (i) A more easily-oxidize(reduced) donor(acceptor) will increase the electron transfer rate; (ii) A longer-lived excited state will decrease the fluorescence rate. The ideal fluorescer will have a short lifetime (the shorter the better), a high quantum yield, a low intersystem crossing rate, energetics so that energy transfer to the anthraquinone is impossible but that electron transfer is fast, be flat so that it intercalates in the hairpin and the duplex without messing up base-pair recognition by hydrogen bonding, absorb where the anthraquinone does not, fluoresce in the "red" region of the spectrum, and it should also be easy to synthesize.

Such ideal fluorescor would give a substantially black background when no nucleic acid to be determined is present and bright fluorescence in the complex of probe and nucleic acid.

In a preferred mode of the method of the present invention, the rate or efficiency of the electron transfer is different in the probe and in the probe when bound to the nucleic acid. In this case the electron donor and acceptor are preferably bound covalently to the same probe molecule, most preferred at a defined, fixed first distance. Upon binding of the probe to the nucleic acid to be determined, the distance of the electron donor and the electron acceptor is altered, preferably increased, thus decreasing the reaction rate of the electron transfer. The first distance and the distance in the complex (second distance) are not preferably designed such that the rate in one of the cases allows the occurrence of a detectable process, like fluorescence, which the other does not (for example in one case the lifetime of the excited state of the fluorescer may be longer than required for electron transfer and in the other case the time required for electron transfer is longer than the lifetime of the excited state). The detectable process will then serve as an indication or measure of the electron transfer and thus of the presence or absence of a nucleic acid to be detected.

A preferred method of the invention therefore is a method wherein the distance between acceptor and donor is a probe is altered upon binding to the nucleic acid, preferably by more than 5 base units in a stack.

In order to evaluate the results from determining of the occurrence of the electronic transfer, one skilled in the art will correlate the signals or results received from experiments wherein the amount or presence of a nucleic acid to be determined is defined. This can then be made by usual calibration experiments, for example, using standard samples containing different specified amounts of nucleic acids to be determined in subjecting the standards to the same conditions as the sample suspected to contain the nucleic acid to be determined. Qualitative and quantitative determination is possible.

An important feature of the formation of the probe-analyte complex is that the distance between the donor and acceptor is relatively fixed.

While these are the core steps of the method of the present invention, this method can be adapted to known convenient formats, for example, by introducing this concept into assays wherein the nucleic acid to be determined is determined in an immobilized state. A very advantageous format of the present invention is disclosed in FIG. 2. In this homogeneous (i.e. single solution) format, the sample containing the nucleic acid to be determined (comp. target DNA) and nucleic acids not to be determined (non-comp. target) in soluble form, the probe molecule containing the electron acceptor and an electron donor are mixed. Only nucleic acids to be determined will hybridize to the specific probe molecule. Nucleic acids not complementary to the probe molecule will not hybridize. Therefore, after inducement of electron transfer, there will be higher or lower light emission from the donor or acceptor if the nucleic acid to be determined was present.

In FIG. 3, the same homogeneous format is described wherein one probe containing an acceptor and another probe containing a donor is used. Only binding of both probes adjacent to each other, whereby the electron transfer is capable of propagating from donor to acceptor will yield a change in light emission.

Figure 4:
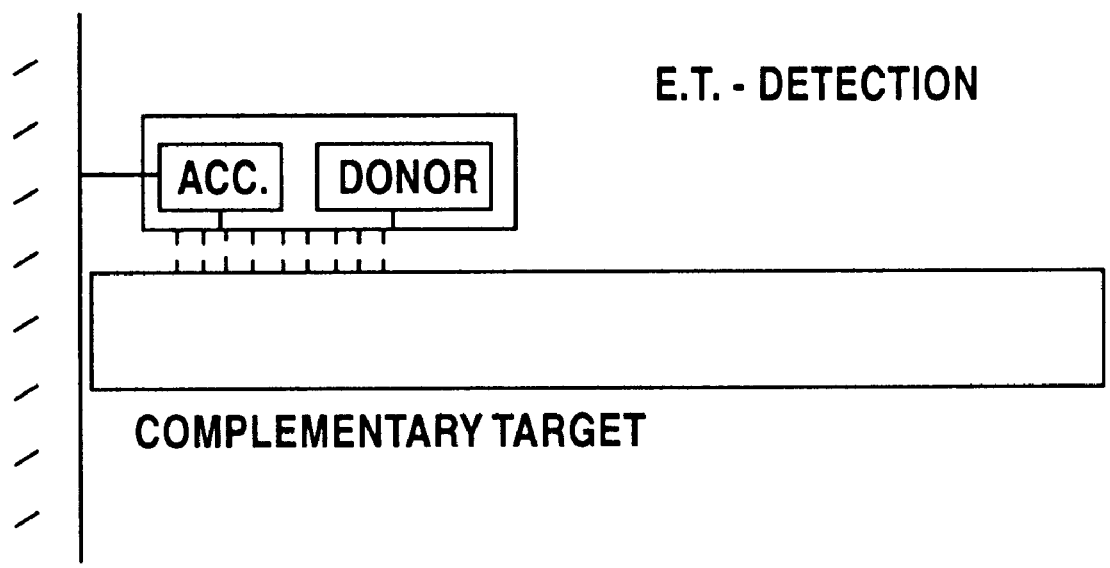
FIG. 4 shows a format using an immobilised probe containing an internally positioned acceptor and donor in the same probe.

In FIG. 4, a heterogeneous assay format is disclosed. The probe molecule containing both an electron acceptor (acc.) and an electron donor (Donor) is bound to a solid phase, for example, a polystyrene surface. This can be accomplished either by covalent bonding or using streptavidin-coated surfaces and biotin-labeled probes. Upon excitation of the electron acceptor, electron transfer is induced on the solid phase, and can be detected by identifying the modified donor only if the nucleic acid to be determined was bound to the solid phase near base-pairing via the immobilized probe molecule. The assay format using an immobilized probe is especially advantageous if the sample contains further ingredients disturbing the irradiation of a detection, for example, by absorbing light in the range of the irradiation or emission wavelength.

In an embodiment the nucleic acid to be determined is bound by nucleic acid analyte probe molecules capable of forming a hairpin structure. In this design, the electron donor (Do) and acceptor (Ac) are initially brought into relatively close proximity by the nature of the hairpin structure (FIG. 6). The close location of the electron transfer moieties will generally lead to high electron transfer rates and efficiencies between these two groups. Thus, spectroscopic changes induced by electron transfer will be pronounced. This could, for instance, be either luminescence initiation or luminescence quenching by electron transfer. A preferred application of this invention is the case when duplex DNA or the DNA-PNA complex of the probe and the nucleic acid to be determined has the characteristic of a bioinsulator. In this case when the hairpin probe is hybridised to a target nucleic acid (e.g. a PCR amplicon) electron transfer rates will be reduced compared with the rate in the probe itself and, therefore, less or no luminescence quenching will be observed from the complex than from the probe.

A hairpin structure is synthesized preferentially in a parallel mode. It consists of two hybridisable segments and a hinge segment (a segment linking the hybridisable segments). The two hybridisable segments are complementary to each other and to two non-overlapping segments of the nucleic acid to be determined. Due to the parallel synthesis of the whole hairpin, the two segments will form an antiparallel duplex. The two hybridisable segments are preferentially composed of 6–12 monomers each, each segment containing an electron transfer moiety capable or not capable of forming hydrogen bonds. The electron transfer moieties are preferentially placed in such a way that they are juxtaposed in the hairpin structure on that one of them is an electron donor and one of them is an electron acceptor. The close positioning of the electron transfer moieties makes electron transfer as optimal as possible. The preferred distance of the electron transfer moieties on different segments is between 1 and 10, more preferably 1 and 5 when the segments are hybridized to each other (a distance of 0 meaning base positions forming hydrogen bonds with each other, if bases were present at this position). The hinge segment is composed of 2–7 monomers, preferentially composed of 3–5 monomers.

In another embodiment the close electronic interaction between the donor and the acceptor is also used (see FIG. 7). In this embodiment the analyte specific probe (PNA2) contains the donor (or the acceptor). A second probe (PNA1) containing the other electron transfer moiety is complementary to a part of the first probe. When these are hybridised the interaction between the acceptor and the donor is as outlined above. When the analyte is introduced to the mixture, the short acceptor probe will be displaced by the analyte thus preventing the electron transfer interaction between the donor and the acceptor. Depending on the choice of donor/acceptor this could lead to either luminescence initiation or quenching.

Further subject matter of the invention are molecules of the general formulae I and II.

The compounds of the general formula I can be used advantageously in the above-disclosed method for determining a nucleic acid in a sample as the nucleic acid analogue probe molecule. These compounds can be prepared analogous to the synthesis described in WO 92/20702, WO 94/25477, WO 96/20212, EP-0 672 677 and EP-0 700 928, just replacing one or more monomers used in the oligomerisation with one ore more monomers containing non-nucleobase containing electron acceptors or non-nucleobase containing electron donors. A preferred way to produce the compounds of general formula I is the step-wise chemical synthesis according to WO 92/20702, incorporating as a monomer a compound of the general formula VIIIa–VIIIc

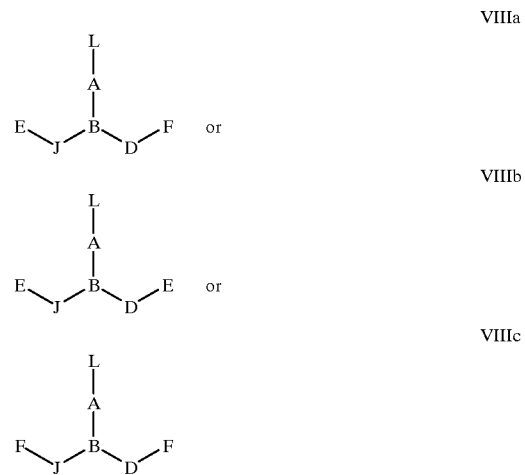

wherein the definitions of A, B, J and D are chosen from the definitions of $A^1$–$A^n$, $B^1$–$B^n$, $J^1$–$J^n$ and $D^1$–$D^n$ in formula I, respectively with the condition that any amino groups therein may be protected by amino protecting groups; E is COOH, CSOH, SOOH, $SO_2OH$ or an activated derivative thereof; F is $NHR^3$ or $NPgaR^3$, where $R^3$ is as defined above and Pga is an amino protecting group and L is a non-nucleobase electron donor or acceptor moiety.

Preferred monomers are amino acids having formula (IX)

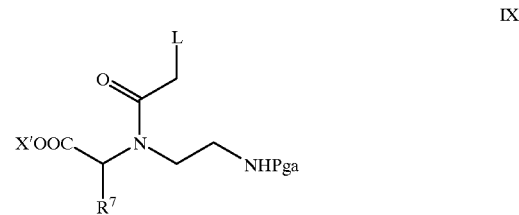

wherein X' is a carboxylic acid protection group or hydrogen, $R^7$ is independently selected from the group consisting of hydrogen and the side chains of naturally occurring alpha amino acids, or amino-protected and/or acid terminal activated derivatives thereof.

Therefore, a preferred method of preparing a molecule of general formula I is characterized in that a molecule of general formula VIIIa–VIIIc or IX wherein X' is hydrogen is reacted with a compound of general formula X

$H_2N$—K (X)

wherein
K is a solid phase, like amino modified glass, or a solid phase bound or free compound of general formula I or II or a compound of formula I in protected form. These compounds can further be modified by attaching monomeric units not containing an electron transfer moiety.

Any reactive groups like primary amino groups or hydroxyl groups are preferably protected by removable or non-removable protecting groups, like benzyloxycarbonyl, Boc or Fmoc if they are not intended to react in the elongation reaction.

The following examples shall explain the invention in more detail using PNA as an example of a probe molecule. The PNA oligomers described above are synthesised by solid phase synthesis procedures. The preferred solid support is polystyrene but also other solid supports such as ®Tentagel and ®Controlled Pore Glass may be used. The synthesis proceeds from the C-terminal position of the PNA and proceeds via couplings of monomers and/or amino acids protected with acid labile protecting groups. Reactive groups on the bases/side chains are also protected. After deprotection of the moiety directly linked to the solid support the subsequent building blocks (monomers/amino acids) are then coupled in the desired sequence. The deprotection of the N-terminal position is performed prior to coupling of the following monomeric unit.

The coupling of the monomeric unit is performed via activation of the carboxylic residue. Such activation is well known to those skilled in this art and, as examples, are: HATU, HBTU, and carbodiimides. The coupling is performed in solvents normally used in peptide chemistry, that is NMP, DMF, acetonitrile, pyridine, dichloromethane or mixtures thereof Activation enhancers such as DMAP may be added. The activated monomeric derivative will be used in excess to the previously deprotected residue and typically in a 2 to 10 times excess. If a high coupling yield is detected (typically >99%) the coupling step will be followed by a capping step, which comprises treatment of the coupled resin bound oligomer with acetic anhydride. The capping mixture comprises 2–20% (v/v) acetic anhydride in NMP/pyridine. If unsatisfactory coupling is detected the coupling step will be repeated to obtain a high coupling yield.

Coupling of a conjugate containing a carboxylic acid can be done analogously to the above described procedure. Other ligands not containing a carboxylic acid can also be linked to the resin bound oligomers. Such other linkages can be performed via isocyanates, isothiocyanates (e.g. fluorescein isothiocyanate), carbonic acid active esters, and sulphonyl chlorides.

The described stepwise synthesis of PNA can be performed manually or automatically. In the latter case commercially available synthesisers (e.g. peptide synthesisers, multiple peptide synthesisers, DNA synthesisers) can be used, provided that the hardware in the instruments is compatible with the chemistry used during the PNA synthesis.

The synthesised oligomer is finally removed from the resin. This is preferentially done by treatment with strong acid, such as TFMSA or HF. The purification of the liberated oligomer is done by HPLC and/or ion exchange. The identity of the pure material is confirmed by mass spectrometry and HPLC.

The letter designation of amino acids and the orientation of PNA follows the traditionally used nomenclature.

EXAMPLES

Abbreviations

Q1 Designates a monomeric unit composed by: 3,6-Diaza-($N^3$-2-anthraquinoyl)-$N^6$-boc-hexanoic acid
Q2 Designates a monomeric unit composed by: 3,6-Diaza ($N^3$-boc-aminoethyl)-4,7-dioxo-7-(2-anthraquinyl)-heptanoic acid
Boc tert-Butyloxycarbonyl
R1 Designates a monomeric unit composed by: 3,7-diaza-($N^3$-boc-aminoethyl)-($N^7$-9-acridinyl)-4-oxo-heptanoic acid
R2 Designates a monomeric unit composed by: 3,10-diaza-($N^3$-boc-aminoethyl)-($N^{10}$-9-acridinyl)-4-oxo-decanoic acid
DCC Dicyclohexylcarbodiimide
DCM Dichloromethane
DIEA Diisopropylethylamine
DMAP Dimethylaminopyridine
DMF Dimethylformamide
ET Electron Transfer
HATU O-(7-Azabenzotriazole-1-yl)-1,1,3,3-tetramethyluronium-hexafluorophosphate
HBTU O-(7-Benzotriazole-1-yl)-1,1,3,3-tetramethyluronium-hexafluorophosphate
HOBT 1-Hydroxybenzotriazole
NMP N-methylpyrrolidinone
NMR Nuclear magnetic resonance
PNA Peptide nucleic acid according to WO 92/20702
TFA Trifluoroacetic acid
TFMSA Trifluoromethanesulphonic acid
HF Hydrogen fluoride
AQ Anthraquinonoes (genus)
Oligomers are designated according to the PNA numbers assigned by PNA Diagnostics.

Example 1

Figure 8:
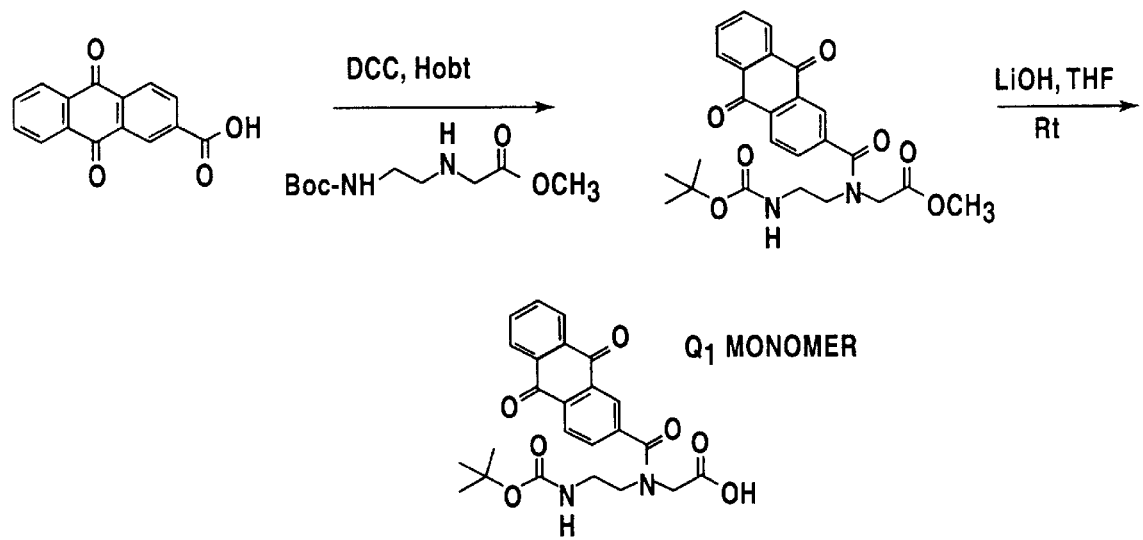
FIG. 8 shows the flow scheme for the preparation of Q1, an electron accepting PNA monomer (linker length l).

Synthesis of 3,6-Diaza-($N^3$-2-anthraquinoyl)-$N^6$-Boc-hexanoic acid ($Q_1$, FIG. 8)

Anthraquinone-2-carboxylic acid (2 g, 7.9 mmol), DCC (1.7 g, 8.3 mmol), HOBT (1.08 g, 8.0 †mmol) and methyl (N-(2-Boc-aminoethyl))glycinate (2 g, 8.6 mmol) were dissolved in DMF (25 mL) and stirred at room temperature overnight. The reaction mixture was filtered and the filtrate was washed with DCM (2×25 mL). The solution was extracted with diluted $NaHCO_3$ (3×25 mL), 2 M $NaHSO_4$ (2×25 mL) and brine. The organic phase was dried with $MgSO_4$, filtered and evaporated to dryness under reduced pressure. The yellow foam was dissolved in THF (10 †mL) and 1 M LiOH (30 mL) was added. The mixture was stirred for 2 h. THF was removed from the solution under reduced pressure and pH was adjusted to 2.8 with 2 M $NaHSO_4$. The precipitate was extracted with DCM (2×25 mL), evaporated to dryness and then redissolved in ethyl acetate (3 mL). The ethyl acetate solution was poured into hexane (150 mL) whereby the target molecule precipitated. Yield 3.1 g (87%).

$H^1$-NMR DMSO-$d_6$ δ: 7.81–8.30 (m, 7 H, aromatics); 6.98 and 7.72 (m, 1 H, BocNH); 4.17 and 3.97 (s, 2 H, $CH_2O$); 3.52 and 3.24 (m, 2 H. CH2); 3.21 and 3.02 (m, 2 H, $CH_2$); 1.17 and 1.19 (s, 9H,Boc).

Example 2

Figure 9:
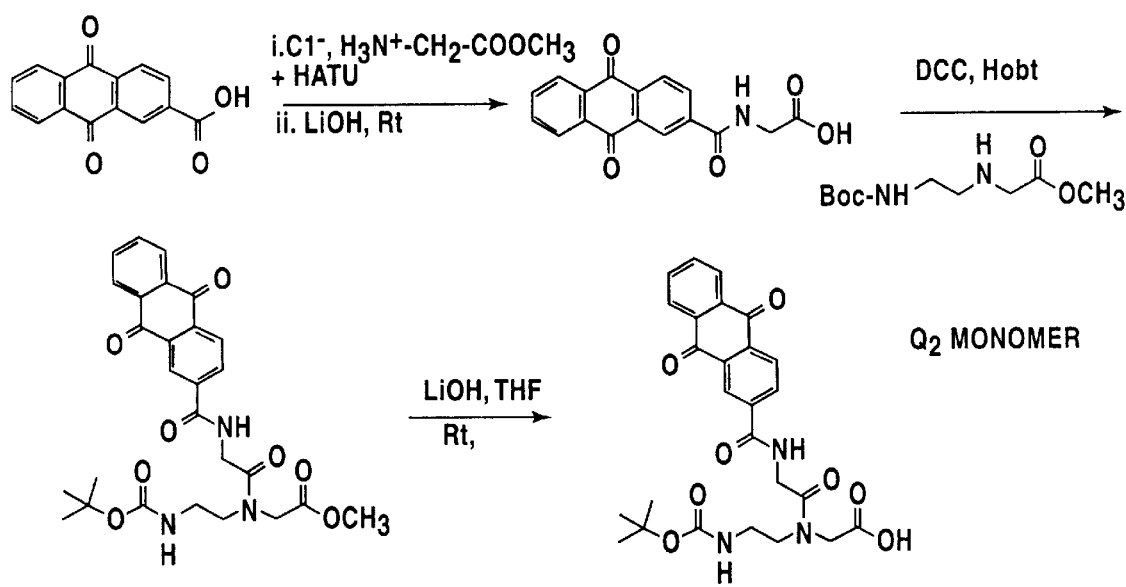
FIG. 9 shows the flow scheme for the preparation of Q2, an electron accepting PNA monomer (linker length 4).

Synthesis of 3,6-Diaza($N^3$-Boc-aminoethyl)-4,7-dioxo-7-(2-anthraquinyl)-heptanoic acid ($Q_2$, FIG. 9)

Methyl 4-(2-anthraquinyl)-4-oxo-3-aza-butanoate

Anthraquinone-2-carboxylic acid (3 g, 11.9 mmol), DIEA (3.1 ml, 24 mmol) and HATU (4.5 g, 11.9 mmol) in DCM (30 mL) was stirred for 10 min at room temperature. Methyl glycinate hydrochloride (1.5 g, 11.9 mmol) was added after which the product started to precipitate. The mixture was stirred for an additional 3 h. The precipitated material was collected by filtration. The volume of the mother liquor was reduced to ⅓ and an additional crop was collected. Yield 3.65 g (93%)

4-(2-Anthraquinyl)-4-oxo-3-aza-butanoic acid

Methyl (2-anthraquinoyl)-3-aza-butanoate (3.65 g, 11.3 mmol) was stirred for 1 h at room temperature in 1M LiOH (20 mL) and THF (3 mL) whereby the starting material dissolved. pH of the solution was adjusted to 2.8 with 2 M $NaHSO_4$ and the target molecule precipitated. The organic solvents were removed from the suspension under reduced pressure and the precipitate was collected by filtration and dried. Yield 3.5 g (100%).

$H^1$-NMR DMSO-$d_6$ δ: 9.37 (t, 1 H, NH); 8.67 (d, 1 H, H-1aq); 8.36 (dd, 1 H, H-3aq); 8.30 and 8.28 (1 H, H-4aq); 8.23 (m, 2 H, H-5 and H-8aq); 7.95 (m, 2 H, H-6 and H-7aq); 4,00 (d, 2 H. $CH_2$).

3,6-Diaza($N^3$-Boc-aminoethyl)-4,7-dioxo-7-(2-anthraquinyl)-heptanoic acid ($Q_2$)

4-(2-Anthraquinoyl)-4-oxo-3-aza-butanoic acid (3.5 g 11.5 mmol), DCC (2.6 g, 12.65 mmol), HOBT (1.7 g, 12.65 mmol) and methyl (N-(2-Boc-aminoethyl)) glycinate (3.2 g, 13.8 mmol) was stirred in DMF (50 mL) at room temperature for 48 h. The reaction mixture was filtered and the residue was washed with DCM (2×30 mL). The organic phase was extracted with diluted $NaHCO_3$ (3×30 mL), 2 M $NaHSO_4$ (2×30 mL), brine, dried with $MgSO_4$ and evaporated to dryness. Crystallization from ethyl acetate gave 4.0 g (67%) of methyl 3,6-Diaza($N^3$-Boc-aminoethyl)-4,7-dioxo-7-(2-anthraquinyl)-heptanoate. The methyl 3-aza-3-(N-2-Boc-amonoethyl)-4,7-dioxo-6-aza-7-(2-anthraquinoyl)-heptanoate was hydrolysed at room temperature in 1 M LiOH and 10% THF. The pH of the solution was adjusted to 2.8 with 2 M $NaHSO_4$ and the target molecule precipitated as an oil. The oil was extracted with ethyl acetate and the organic phase was dried with $MgSO_4$. The volume was reduced to 2 mL and hexane (250 mL) was added with stirring, whereby 3-aza-3-(N-2-Boc-amonoethyl)-4,7-dioxo-6-aza-7-(2-anthraquinoyl)-heptanoic acid precipitated. Yield 3.7 g (92%).

$H^1$-NMR DMSO-$d_6$ δ: 12.64 (s, 1 H, COOH); 9.14 (m, 1 H. NH); 8.69 (d, 1 H, H-1aq); 8.67 and 8.35 (dd, 1 H, H-3aq); 8.32 and 8.30 (dd, 1 H, H-4aq); 8.25 (m, 2 H, H-5 and H-8aq); 7.96 (m, 2†H, H-6 and H-7aq); 6.90 and 6.75 (t, 1 H, BocNH); 4.24 (d, 2 H, $CH_2CO$); 4.24 and 4.12 (dd, 2 H, $CH_2CO$); 3.90 (s, 2 H, $CH_2CO$); 3.44, 3.17 and 3.06 (m, 2 H, $CH_2$); 1.40 and 1.38 (s, 9 H, Boc).

Example 3

Synthesis of $R_1$ (FIG. 10)

9-(2-Carboxyethyl)aminoacridine

β-Alanine (1 g, 11.2 mmol) was added to a solution of 9-phenoxyacridine (2.7 g, 10 mmol) in phenol (15 g). The suspension was stirred at 120° C. for 2 h. The solution was cooled to room temperature and poured into ether whereby the product precipitated as a yellow-green solid. It was triturated with hot ethanol, filtered and then washed with ethanol, giving crude 9-(2-carboxyethyl)aminoacridine. Yield 1.9 g (71%).

$H^1$-NMR DMSO-$d_6$ δ: 8.27 (d, 2 H, acr. 1,8); 7.59 (m, 4 H, acr. 2,3,6,7); 7.26 (m, 2 H, acr. 4, 5); 4.05 (t, 2 H, $CH_2CO$); 2.82 (m, 2 H, $CH_2N$). $C_{16}H_{14}N_2O_2$: calc/found: 266/266.

3,7-diaza-($N^3$-Boc-aminoethyl)-($N^7$-9-acridinyl)-4-oxo-heptanoic acid ($R_1$)

A mixture of 9-(2-caboxyethyl)aminoacredine (1.7 g 6.4 mmol), DEA (1.8 g 13.8 mmol) and HATU 2.68 g, 7 mmol) was stirred in DMF (40 ml) at room temperature for 10 min. Methyl-Boc-aminoethylglycinate (1.8 g, 7.8 mmol) was added and the solution was stirred at 60° C. for 4 h. The solution was cooled and DCM (100 ml) was added. Subsequently the solution was extracted with 0.5 M $NaHCO_3$ (3×40 ml), 2 M $NaHSO_4$ (2×40 ml) and brine. The organic fase was dried with $MgSO_4$ and evaporated yo dryness. The residue was dissolved in THF/1 M LiOH (2/10) 60 ml The pH of the solution was ajusted to 2.8 with $NaHSO_4$ wheby an oil precipitated. The waterfase was decanted off and the oil was dissolved in ethanol (10 ml). The solution was purred into ether and 3,7-diaza-($N^3$-Boc-aminoethyl)-($N^7$-9-acridinyl)-4-oxo-heptanoic acid ($R_1$) precipitated. Yield 2.3 g (77%)

H1-NMR DMSO-d6 δ: $C_{16}H_{30}N_4O_5$: 8.50 (dd, 2 H. acr. 1, 8); 7.91 (m, 2 H, acr. 2, 7); 7.84 (m, 3 H, acr. 3,6 and 9 NH); 7.49 (m, 2 H, acr. 3,6); 6.89 and 6.76 (m, 1 H, BocNI); 4.28 (m, 2 H, $CH_2CO$); 4.05 and 3.92 (s, 2 H, $CH_2CO$); 2.82 (m, 2 H, $CH_2N$). $C_{25}H_{30}N_4O_5$: calc/found: 466/466

Example 4

Figure 11:
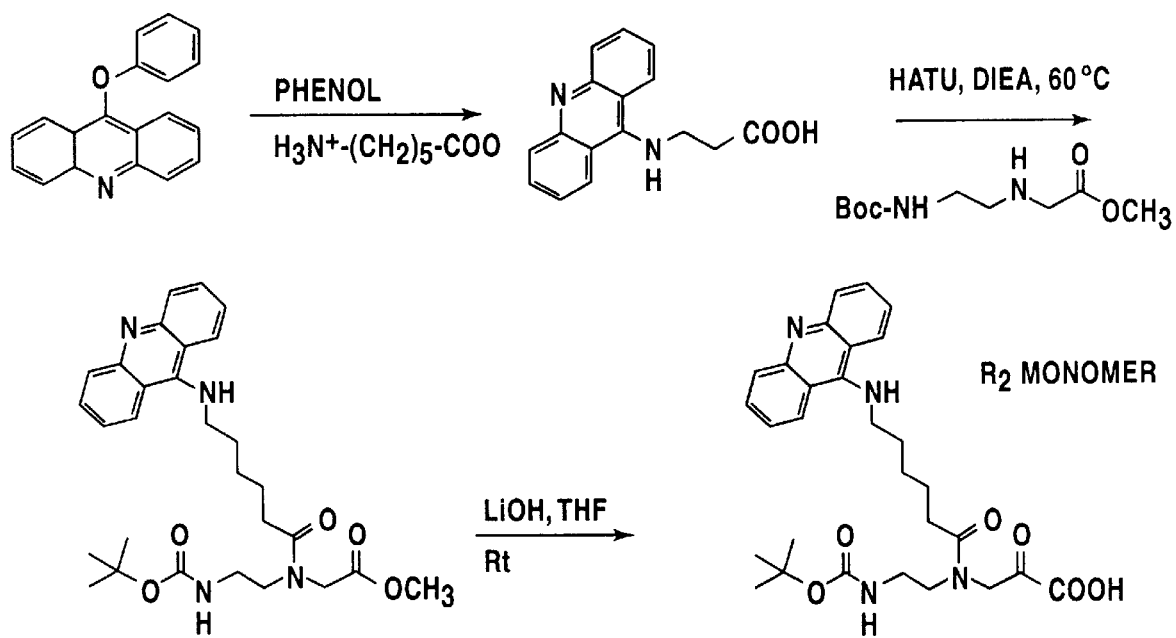
FIG. 11 shows the flow scheme for the preparation of R2, an electron donating PNA monomer (linker length 7).

Synthesis of 3,10-diaza-($N^3$-Boc-aminoethyl)-($N^{10}$-9-acridinyl)-4-oxo-decanoic acid ($R_2$, FIG. 11)

9-(5-Carboxypentyl)-aminoacridine

6-Aminohexanoic acid (1.47 g, 11.2 mmol) was added to a solution of 9-phenoxyacridine (2.7 g, 10 mmol) in phenol (15 g). The suspension was stirred at 120° C. for 2 h. The solution was cooled to room temperature and poured into ether whereby the product precipitated as a yellow-green solid. It was triturated with hot ethanol, filtered then washed with ethanol, giving crude 9-(5-carboxypentyl) aminoacridine.Yield 2.4 g (78%).

$H^1$-NMR DMSO-$d_6$ δ: 8.27 (d, 2 H, acr. 1, 8); 7.61 (m, 4 H, acr. 2,3,6,7); 7.26 (m, 2 H, acr. 4, 5); 3.79 (t, 2 H. $CH_2CO$); 2.16 (t, 2 H, $CH_2N$); 1.72, 1.50 and 1.37 (m, 2 H, $CH_2$). $C_{19}H_{20}N_2O_2$: calc/found: 308/308

3,10-diaza-($N^3$-Boc-aminoethyl)-($N^{10}$-9-acridinyl)-4-oxo-decanoic acid ($R_2$)

A mixture of 9-(5-carboxypentyl)aminoacridine (1 g, 3.2 mmol), DIEA (0.9 g, 6.9 mmol) and HATU (1.34 g, 3.5 mmol) was stirred at room temperature for 10 min in DMF (30 mL). Methyl-Boc-aminoethylglycinate (0.9 g, 3.8 mmol) was added and the solution was stirred at 60° C. for 4†h. The solution was cooled and DCM (60 mL) was added. Subsequently the solution was extracted with 0.5 M $NaHCO_3$ (3×30 mL), 2 M $NaHSO_4$ (2×30 mL) and brine. The organic phase was dried with $MgSO_4$ and evaporated to dryness. The residue was dissolved in TBF/1M LiOH (2/10) (40 mL). The pH of the solution was adjusted to 2.8 with $NaHSO_4$ whereby an oil precipitated. The water phase was decanted off and the oil was dissolved in ethanol (5 mL). The solution was then poured into ether and 3N-(Boc-aminoethyl)-10N-(9-acridinyl)-3,10-diaza-4-oxy-nonanicacid precipitated. Yield 1.2 g (76%).

$H^1$-NMR DMSO-$d_6$ δ: 8.51 (d, 2 H, acr. 1, 8); 7.90 (m, 2 H, acr. 2, 7); 7.82 (m, 2 H, acr.3, 6); 7.71 (m, 1 H, NH); 6.83 and 6.45 (m, 1 H, BocNH); 7.51 (m,2 H, acr. 4, 5); 4.01 (m, 2 H, $CH_2CO$); 3.98 and 3.88 (s, 2 H, $CH_2CO$); 3.23, 3.00, 2.30, 2.03 and 1.88 (m, 2 H,CH$_2$); 2.16 (t, 2†H, CH$_2$N); C$_{27}$H$_{36}$N$_4$O$_5$: calc/found: 508/508.

Example 5

Synthesis of 3,6-Diaza-(N$^3$-acetyl, N$^6$-Boc)-hexanoic acid

To a solution of methyl N-(3oc-aminoethyl)glycinate (2 g, 8.6 mmol) in DCM (30 mL) was added acetic anhydride (0.9 g, 8.8 mmol) and pyridine (1 mL). The mixture was stirred at room temperature for 2 h. The reaction was extracted with 0.5 M NaHCO$_3$ (3×30 mL), 2 M NaHSO$_4$ (2×30 mL) and brine. The organic phase was dried with MgSO$_4$ and evaporated to dryness. The residue was dissolved in THF/LiOH (1M) 2/10 (40mL) and stirred for 1 h after which the pH was adjusted to 2.8 with NaHSO$_4$. The solution was extracted with ethyl acetate and the organic phase was dried with MgSO$_4$; 3,6-diaza-(N$^3$-acetyl, N$^6$-Boc)-hexanoic acid was collected by evaporation to dryness. Yield 1.8 g (82%).

H$^1$-NMR DMSO-d$_6$ δ: 12.31 (s, 1 H, COOH); 6.83 and 6.69 (t, 1 H, BocNH); 4.07 and 3.89 (s, 2†H, CH$_2$CO); 3.30 (m, 2 H, CH$_2$); 3.09 (m, 2 H, CH$_2$); 2.00 and 1.89 (s, 3 H, CH$_3$); 1.37 (s, 9 H, Boc).

Example 6

Synthesis of PNA Oligomers

The monomers described above were essentially incorporated by the oligomerisation procedure previously described and what has been disclosed in WO 92/20702. However, the PNA syntheses containing the donor moieties constituted a special case because the capping step was omitted in the part of the synthesis including and following the donor monomer. However, to obtain high coupling yields the monomeric moieties of this part of the synthesis was double coupled. Later experiments have shown that capping may be used during oligomerisation of donor containing molecules. All oligomers were cleaved from the resin by TFMSA and subsequently HPLC purified. The identity was confirmed by mass spectroscopy (MALDI-TOF).

PNA 554: calc./found: 5237/5239
PNA 555: calc./found: 5469/5467
PNA 579: calc./found: 5429/5426
PNA 586: calc./found: 5336/5333
PNA 626: calc./found: 6631/6636
PNA 627: calc./found: 6563/6564

Example 7

Estimation of PNA Concentrations

Concentrations of PNA stock solutions were estimated by UV absorbance at 260 mn. The extinction coefficients of the PNA oligomers were calculated using the nearest neighbour values for DNA, with Adenine substituted for Q or R. (Because of the length of the PNA oligomers, the error introduced by this substitution will be negligible.) In a typical measurement, PNA was dissolved in water and the absorbance at 260 nm was measured after incubation for 5 minutes at 75° C. in order to minimise secondary structure in the PNA. (Extinction coefficients determined from room temperature absorbance measurements tend to be 5–10% lower than those measured at the higher temperature). DNA oligomers were purchased from Midland Certified Reagent Company.

Example 8

Formation of Stable PNA/DNA Hybrids: Thermal Denaturation Studies

This example demonstrates the ability of PNAs containing an electron acceptor to hybridize with complementary DNA oligomers.

Samples were prepared consisting of equimolar concentrations of PNA and DNA oligomers (1.0 or 2.0 μM each) in 1.0 mL of 10 mM sodium phosphate buffer (pH=7.0). The PNA strand will often precipitate upon addition of the phosphate, presumably due to complexion of the lysine units by the phosphate. Mixing and addition of the DNA strand results in dissolution of the PNA. Samples were placed in cuvettes (1.5 mL capacity, 1.0 cm pathlength) and sealed with tape to prevent evaporation of water during heating/cooling cycles. The absorbance of the samples at 260 nm was monitored as a function of temperature for three consecutive runs: heating at 1.0° C./min, and cooling at 0.5° C./min and heating again at 0.5° C./min. In two experiments the absorbance was monitored at 330 nm, where the AQ unit absorbs. Due to the low extinction coefficient of the AQ, these experiments were performed at 20 μM each of PNA and DNA.

Data were analysed by exporting as an ASCII file and importing into a standard graphics software. The absorbance was plotted versus temperature for each sample. Melting temperatures (T$_m$) were determined as the maxima of plots of the first derivative of absorbance with respect to temperature, assuming a first order phase transition. T$_m$ values given in the text and tables have error values of ±0.5° C.

An initial question to address regarded what could be tolerated on the DNA strand at the central site, i.e. directly across from the AQ in the hybrid. Five variations were considered: (1) An abasic site (X) was incorporated into the oligomer. This residue replaces the standard DNA base with a hydrogen atom at carbon-1 of the deoxyribose moiety and would be expected to provide the most room for accommodation of the AQ within the duplex. (2)–(5) Each of the four DNA bases: G, A, C and T were incorporated into the sequence. These DNA oligomers are identified as DNA579Z, where Z=X (Abasic), G, A, C, and T, respectively.

DNA: 5'-TCG-CTG-GAA-Z-AAG-GTA-GGA-3' (SEQ ID NO:1)

DNA579Z

PNA: H-Lys-Lys-TCC-TAC-CTT-Y-TTC-CAG-CGA-Gly-NH$_2$ (SEQ ID NO:2)

PNA554: Y=Acetyl

PNA579: Y=Q1

PNA586: Y=Q2

The PNA579/DNA579X hybrid melts with high cooperativity at T$_m$=61.4° C. (FIG. 12). There is no hysteresis in the transition indicative of rapid hybridisation kinetics as previously observed for full-length 1:1 PNA-DNA duplexes. The PNA586/DNA579X hybrid melts at 68.3° C., approximately seven degrees higher than for PNA579. The greater stabilization for PNA586 could be due to the increased flexibility which arises from the longer linker connecting the AQ to the PNA backbone. In both cases, the T$_m$ is significantly higher than when the PNA bears only an acetyl group at the central position, indicating that the AQ moiety stabilizes the PNA/DNA hybrid (Table 1).

Monitoring the T$_m$ at 330 nm, where only the AQ unit absorbs light, reveals monophasic transitions for both PNA/DNA hybrids (FIG. 12). The hyperchromicity observed for the PNA586/DNA579X hybrid is nearly twice as great as that for the PNA579/DNA579X hybrid, consistent with a structure in which the AQ unit is intercalated into the duplex and that insertion of the AQ is more favorable for the longer linker.

TABLE 1

Effect of AQ Linker Length on PNA/DNA Hybrid Stability

| PNA | [Duplex] ($\mu$M) | Wavelength(nm) | $T_m$(° C.) | % Hypochromicity |
|---|---|---|---|---|
| 554 | 1.0 | 260 | 56.6 | 16.5 |
| 579 | 1.0 | 260 | 61.4 | 13.5 |
| 586 | 1.0 | 260 | 68.3 | 15.5 |

The PNAs form stable hybrids with the DNA579Z oligomers in which Z=G, A, C or T (Table 2). The resulting hybrids are only slightly less stable than the corresponding duplexes with Z=X.

TABLE 2

Effect of Opposed Base on PNA/DNA Hybrid Stability ($T_m$ given in ° C.)

| Base | PNA554 | PNA579 | PNA586 |
|---|---|---|---|
| X | 56.6 | 61.4 | 68.3 |
| G | 55.6 | 59.2 | 65.9 |
| A | 57.3 | 59.7 | 66.6 |
| C | 55.8 | 59.7 | 67.1 |
| T | 56.8 | 59.5 | 67.4 |

Effect of Single Mismatches

PNA555 is analogous to PNA579 with the exception of replacing with G at position 7. Hybridisation of this PNA with its abasic DNA complement (DNA555X) yields a duplex which melts at 63.1° C. The 2° C. stabilisation relative to PNA579/DNA579X could reflect greater base stacking in the region of the C-7 (PNA)/G-32 (DNA) base pair. Hybridisation of PNA555 with DNA579 yields a duplex which possesses a G-G mismatch and melts at 53.4° C. Thus, a single mismatch depresses $T_m$ by 8–10° C.

Effect of PNA Orientation on Hybrid Stability

The preferred orientation of PNA/DNA duplexes is antiparallel, where the PNA N-termini are aligned with the DNA 3'-termini. If the PNA579 sequence is inverted, hybridization with DNA579 produces a duplex which melts at 49.9° C. Thus, parallel orientation of the PNA and DNA strands results in reduction of the $T_m$ by ca. 11° C.

These experiments demonstrate that the DNA recognition properties of the PNA(AQ) conjugates are completely analogous to those of unmodified PNA strands. While the stability of the resulting duplexes are most likely lower than would be observed for a 19 base pair PNA-DNA hybrid (due to the lack of base-pairing at the central AQ position), the presence of the AQ moiety stabilises the duplex by >4° C. relative to the case where both strands contain abasic residues at the central position, indicative of a strong interaction (stacking) between the AQ and the duplex.

Example 9

Detection of Electron Transfer within PNA/DNA Hybrids by Photocleavage Assay

This example describes the ability of the PNA containing an anthraquinone (AQ) to initiate photocleavage of the DNA strand within a hybrid duplex by photoinduced electron transfer.

Photocleavage of the DNA strand within PNA-AQ/DNA hybrids was studied using radiolabelled DNA and polyacrylamide gel electrophoresis (PAGE). Synthetic DNA oligomers were labelled at the 5'-OH terminus using [$\gamma$-$^{32}$P]-ATP and T4 polynucleotide kinase according to standard procedures. 5'-endlabelled oligomers were purified by 20% denaturing PAGE and precipitation. Samples were prepared for irradiation by mixing 5.0 $\mu$M each of PNA and unlabelled DNA as well as labelled DNA (2000–4000 cpm per sample) in 10 mM sodium phosphate buffer (pH=7.0). This ensures that there will be a slight excess of DNA over PNA, minimising contributions from unhybridised PNA. Samples were heated to 85° C. for 5 min then allowed to cool to room temperature. In cases where the only difference in samples would be the irradiation time, a single sample was prepared by this procedure and irradiated, with aliquots removed at the desired times.

Irradiation was performed using a Rayonet photoreactor equipped with 8 lamps ($\lambda_{max}$=350 nm). Samples were placed in microcentrifuge tubes and suspended parallel to the lamps via a rotating sample holder. While most of the exciting light is either not incident on the tubes or scattered by them, the tubes are sufficiently transparent at 330 nm to permit photocleavage to proceed in reasonable times (less than one hour).

For experiments involving methylene blue, PNA-DNA hybrids were prepared as described above, then methylene blue was added to give 10 or 20 $\mu$M concentration. Samples were irradiated for 15 min using the filtered ($\lambda$>600 nm) output of a 150 W Hg arc lamp.

For experiments in which $D_2O$ was substituted for water, all of the components (PNA, DNA, buffer, methylene blue where desired) were mixed, then the water was evaporated under vacuum. 20 $\mu$l $D_2O$ was added to the samples and then removed by evaporation. This procedure was repeated, then the samples were finally dissolved in the appropriate amount of $D_2O$. An identical procedure was followed using $H_2O$ for control samples.

After irradiation, the salt concentration was increased by addition of sodium acetate (pH=5.2) to 0.3 M, and magnesium chloride to 10 mM in a total volume of 50 $\mu$L. 100 $\mu$L cold ethanol was added and after vortexing, samples were placed on dry ice for 30 min. followed by centrifugation at 12,000 g for 30 min. The supernatant was discarded and the pellet washed with 80% ethanol prior to drying. Samples were either then suspended in denaturing loading buffer or incubated with 100 $\mu$L piperidine (1 M) for 30 min at 90° C. After the piperidine was removed by vacuum evaporation, the DNA was dissolved in 20 $\mu$L water which was then evaporated. This procedure was performed once more and then the DNA was suspended in denaturing loading buffer. DNA fragments were ultimately separated on a 20% denaturing polyacrylamide gel and cleavage sites were visualised by autoradiography.

Figure 13:
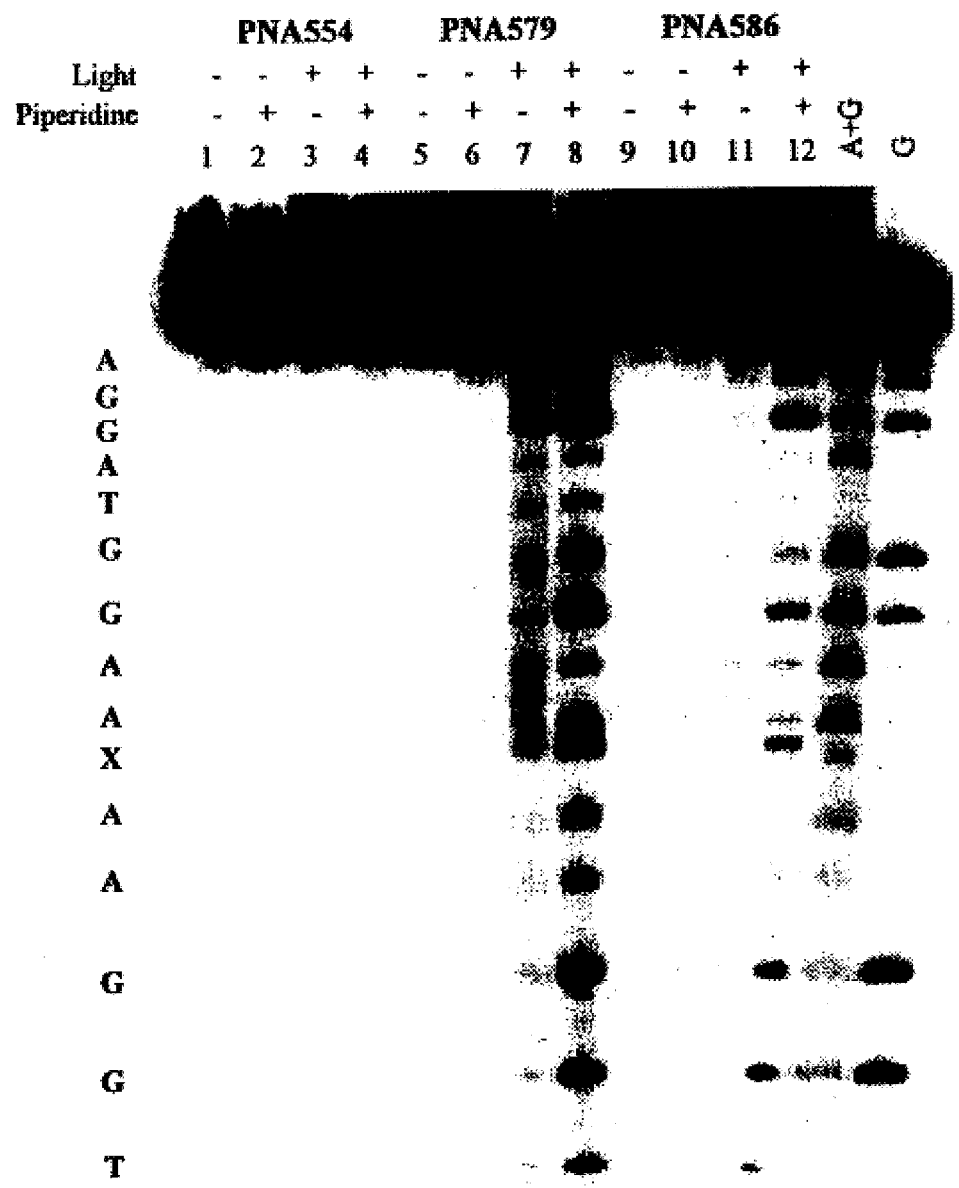
FIG. 13 shows photoinduced cleavage of DNA within PNA/DNA hybrids.

Irradiation of a PNA579/DNA579X duplex with 350 nm light for one hour led to very little spontaneous degradation of the DNA. However, after piperidine treatment, strong cleavage is observed at several positions (FIG. 13, Lane 8). Cleavage is not observed for a PNA554/DNA579X hybrid, which lacks an AQ moiety (Lane 4). The main cleavage sites are the three GG steps as well as the abasic site at the center of the duplex. Previous work has shown that irradiation of DNA-intercalated AQ leads to piperidine-dependent cleavage with high selectivity at the 5'-G of GG doublets. It has unambiguously been shown in the literature (Breslin, D. T. and Schuster, G. B. J. Am. Chem. Soc. 1996, 118, 2311–2319) that this GG-selective cleavage of DNA is initiated by photoinduced electron transfer from the DNA bases to the excited state AQ. The similar selectivity observed in FIG. 13 suggests that the AQ reacts similarly with the PNA/DNA hybrid.

For the two GG sites on the 3' end of the duplex, cleavage at the 5' G is favored over that at the 3' G. Thus, the two GG sites oriented in the 3' direction relative to the AQ exhibit the same 5'-dependent cleavage as observed in duplex DNA. However, cleavage at the GG step on the 5'-side of the AQ is distributed evenly between the two sites. The 5'-vs 3'-distribution of cleavage at the GG step has been proposed to depend on the angle of rotation between the two guanines as they stack atop one another (Sugiyama, H. and Saito, I., J. Am. Chem. Soc. 1996, 118, 7063–7068). However, it is important to note that trapping requires not only a significantly lower oxidation potential at the GG site but also a chemical reaction to prevent the electron and hole from recombining. This step involves addition of either water or oxygen to the guanine radical cation, a process which will be influenced by the exposure of the base to solvent. It has been noted that the bases in PNA-DNA hybrids are closer to the exterior of the helix than in B-form DNA. NMR (Erikkson, M.; Nielsen, P. E. Nature Struct. Biol. 1996, 3, 410–413) and x-ray diffraction data (Betts, L.; Josey, J. A.; Veal, J. M.; Jordan, S. R. Science 1995, 270, 1838–1841) indicate that the degree of inter- and intrastrand stacking within PNA-DNA hybrids is highly sequence dependent. Thus there is no reason to expect that the GG cleavage will exhibit the same 5'-preference as observed in duplex DNA. This is supported by the cleavage data on PNA/DNA hybrids disclosed in this invention.

Experiments were performed with PNA586/DNA579X which were analogous to those performed with PNA579. The results for the longer linker are similar to the shorter linker: After piperidine treatment, cleavage is observed at all three GG sites as well as at the abasic site (FIG. 13, Lane 12). The 5'-G is clearly favored for the two sites which are on the 3'-side of the abasic site while the two Gs are cleaved approximately equally at the other GG site. One notable observation is that the cleavage efficiency for the longer linker connecting the AQ to the PNA backbone is significantly lower than for the shorter linker.

It is clear that the cleavage is occurring at positions which are far from the AQ. In particular, the distal GG step in the 3' direction is ca. 22 Å away from the AQ within the hybrid (based on a rise of 3.6 Å per base pair). Even if the AQ were able to adopt extrahelical conformations, the short linker connecting it with the backbone precludes direct reaction between the AQ and the remote G sites. We next investigated the possibility that the AQ was generating a freely diffusible species. If the PNA and DNA strands are annealed in the presence of a tenfold excess of unlabeled DNA579X the cleavage is completely eliminated. However, if the annealing is performed in the presence of an excess of unlabeled, non-complementary DNA, no effect on the cleavage is observed. This rules out the possible intermediacy of a freely diffusing cleavage agent. Additionally, if the excess unlabeled DNA579X is added after annealing but prior to irradiation, minimal attenuation of the cleavage is observed. This indicates that the PNA/DNA hybrid is thermally stable throughout the irradiation time. These experiments demonstrate that the cleavage arises from excitation of AQ moiety and that the damage is localised at the same duplex wherein the photon is absorbed.

Selective cleavage at G residues by photonucleases in duplex DNA is typically the result of either electron transfer chemistry or singlet oxygen, which can be generated by triplet state molecules. We tested for the involvement of singlet oxygen by comparing the cleavage efficiencies for PNA/DNA hybrid in the presence of $D_2O$ with $H_2O$. (The lifetime of singlet oxygen is increased nearly tenfold in the presence of $D_2O$, leading to significantly enhanced cleavage by singlet oxygen generators). There is no enhancement of cleavage for the sample irradiated in $D_2O$, arguing against a role for singlet oxygen in the mechanism. We also studied cleavage of the DNA strand in the PNA/DNA hybrid using a known singlet oxygen generator, methylene blue. Irradiation with visible light ($\lambda$>600 nm) results in selective cleavage at the guanine residues with a pattern which is similar to that of the AQ-sensitised cleavage. However, this chemistry is strongly enhanced when $D_2O$ is substituted for $H_2O$.

At first consideration, the similar cleavage patterns observed for direct irradiation of the AQ and for singlet oxygen generation by methylene blue would suggest that the quinone-mediated cleavage also involves singlet oxygen. However, the lack of inhibition by non-specific DNA demonstrates that cleavage is not mediated by freely diffusing singlet oxygen. The only way that singlet oxygen could be responsible for the cleavage is if it is generated by the AQ at the central position of the duplex, then diffuses one-dimensionally along one of the grooves in either direction until it reacts with a guanine. The different intensities observed for various Gs would then reflect access of the base to the singlet oxygen molecule. Such a process should exhibit a distance dependence, however, since the first GG step in the 3'-direction would be expected to be a barrier to cleavage at the distal GG step. The equal cleavage observed at these two sites is clearly inconsistent with such a mechanism. Further evidence against a singlet oxygen dependent mechanism comes from the observation that anthraquinone-2-sulfonate, which is freely diffusing in solution, does not induce cleavage of the PNA-DNA hybrid. It is unlikely that the covalently linked AQ can generate singlet oxygen when the unbound AQ cannot, particularly in light of the strong phosphorescence quenching (see Example 10) within the duplex. A further argument against singlet oxygen derived cleavage comes from densitometric analysis of the ratio of cleavage at the 5' and 3' guanine residues in the distal GG site toward the 3' end of the duplex. For the AQ-initiated cleavage, this ratio is 1.40, whereas for methylene blue it is 0.69. If the same intermediate were responsible for the DNA damage, then the ratio of 5'/3' cleavage should be the same for AQ and methylene blue.

Figure 14:
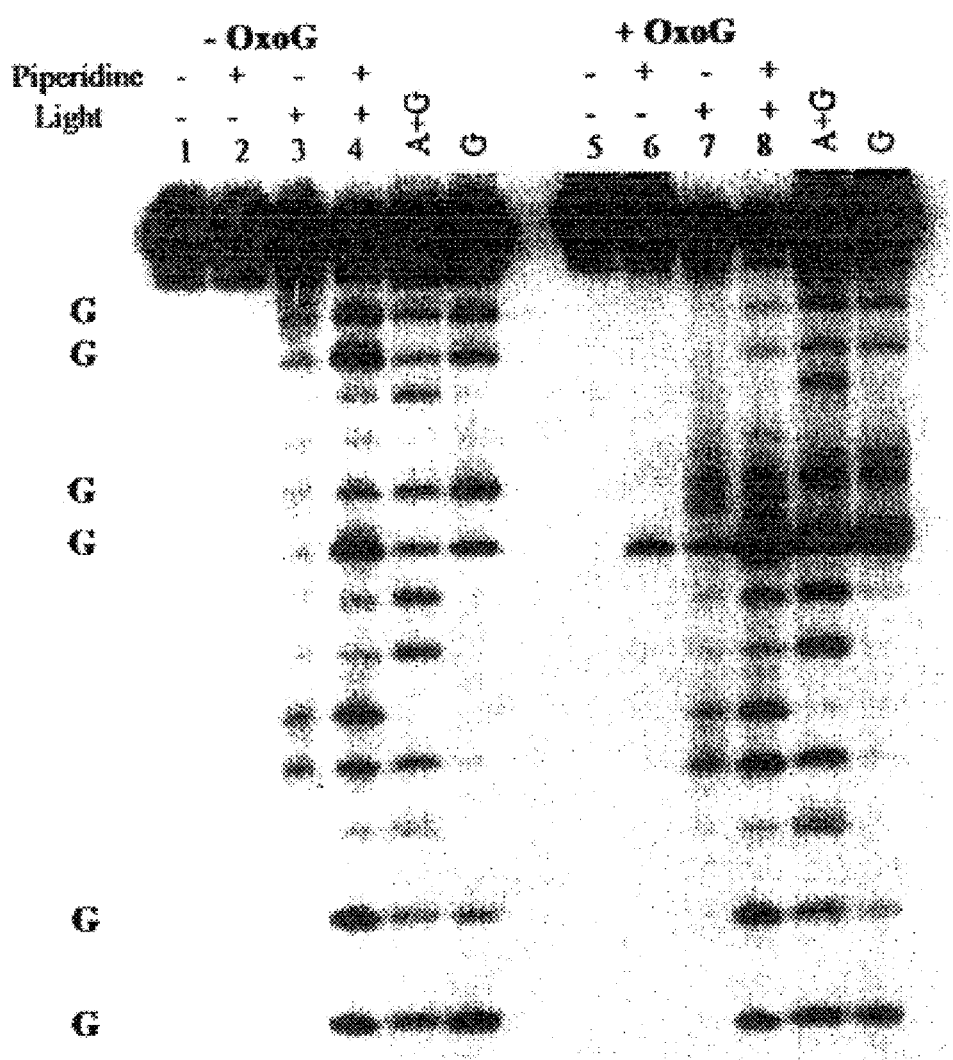
FIG. 14 shows photoinduced cleavage of DNA with an 8-OxoG site.

In light of the preceding discussion, the only explanation for the observed cleavage is electron transfer in the PNA/DNA duplex. The AQ triplet is quenched by electron transfer from an adjacent base, resulting in the injection of a hole within the duplex. This hole can subsequently migrate through the helix until it is trapped at a GG site (see FIG. 5). Incorporation into the duplex of a "trap" site, i.e. a site with an even lower oxidation potential than GG, should significantly alter the cleavage efficiency at the GG sites. The guanine oxidation product, 7,8-dihydro-8-oxoguanine (8-OxoG) was chosen as a potential trap site since its oxidation potential is estimated by Sheu and Foote to be ca. 0.4 V lower than that of guanine (Sheu, C.; Foote, C. S. J. Am. Chem. Soc. 1995, 117, 6439–6442). DNAS79T(OxoG) is analogous to DNA579T except that G-13 is replaced by 8-OxoG. This DNA was radiolabeled on the 5'-terminus according to standard procedures, then hybridized with PNA579 and irradiated. After piperidine treatment, a significant enhancement is observed in the cleavage at the 8-OxoG position, while cleavage at the distal GG site is significantly suppressed relative to the case where a normal G is present at position 13. (See FIG. 14, compare lanes 8 and 4). This observation is consistent with a model in which the excited state AQ accepts an electron from an adjacent base at the intercalation site, injecting a hole into the PNA/DNA helix. This hole migrates along the helix by a series of discrete electron transfers until it reaches a GG site where it can be trapped by reaction with water or oxygen. The (8-OxoG)G site is a more effective trap than is a normal GG site, inhibiting migration of the hole to the distal GG site. Significantly, cleavage at the GG site in the other direction is unaffected by the 8-OxoG.

Example 10

Evidence for Photoinduced Electron Transfer from Low Temperature Phosphorescence Experiments This example uses phosphorescence spectroscopy to study the reaction of the excited state AQ with the PNA/DNA hybrid.

Phosphorescence emission was measured as an indication of electron transfer from the bases of the hybrid to the photoexcited AQ, since electron transfer quenches this emission. (The quantum yields for phosphorescence are sufficiently low that the samples have to be prepared in a frozen glass matrix in order to be able to detect the phosphorescence. The matrix used was 30% ethylene glycol in 10 mM phosphate buffer, pH=7.0. Stable hybrids are formed even in the presence of the glycol as evidenced by a suppression of the $T_m$ of less than 5° C.) Samples were prepared consisting of AQC(2) (a water soluble AQ), or PNA-AQ alone or with complementary DNA. In each case, the concentration of AQ (linked or unlinked to PNA) was 5.0 $\mu$M, as was the DNA concentration for the last sample. Samples were prepared in 10 mM sodium phosphate buffer (pH=7.0) and 30% ethylene glycol, which is required in order to form a low-temperature glass. For PNA/DNA hybrids, samples were heated to 85° C. for 5 min then allowed to cool to room temperature prior to addition of ethylene glycol. Samples (400 $\mu$l) were added to NMR tubes, shaken to position the liquid at the bottom of the tube, then frozen in liquid nitrogen. Phosphorescence spectra were recorded over the spectral region of 400–600 nm with excitation at 330 nm. Slits were set at 5.0 mm on both monochromators to maximise the signal intensity. Spectra were plotted after subtraction of the baseline recorded with a frozen glass lacking AQ and normalisation at 400 nm.

Figure 15:
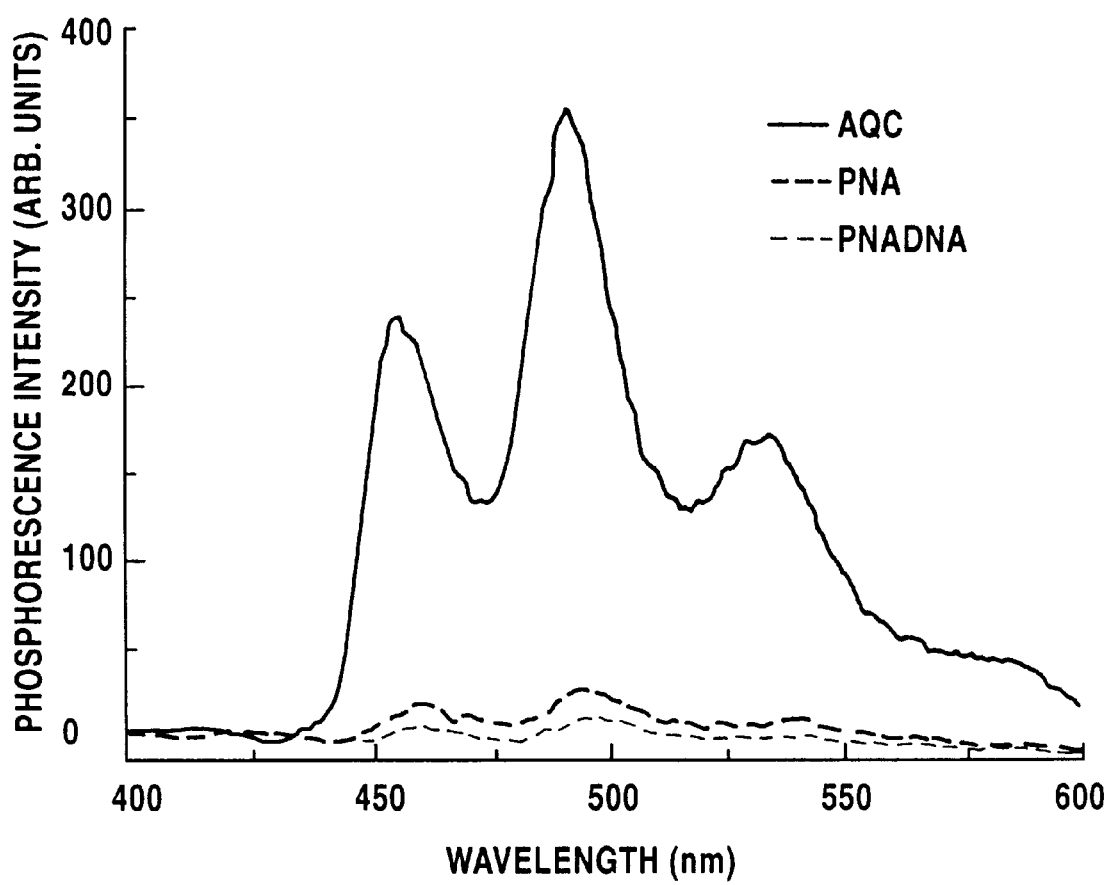
FIG. 15 shows phosphorescence quenching in PNA/DNA hybrids due to electron transfer.

Emission spectra were recorded for three cases: (i) water soluble AQ in the absence of PNA and DNA, (ii) single-stranded PNA, and (iii) PNA-DNA hybrids. For PNA579, the phosphorescence is quenched by ca. 70% and >90% in the single-strand and hybrid forms, respectively, relative to the free AQ. Meanwhile, for PNA586, the phosphorescence is quenched by >90% in both the single-stranded and hybrid forms. (Data for PNA586 are plotted in FIG. 15.) These results indicate that there is efficient photoinduced electron transfer from the bases to the AQ in the hybrid. Moreover, electron transfer is also quite efficient in the single-stranded form, indicating the AQ moiety is capable of reacting with the PNA bases as well as the DNA bases.

Example 11

DNA Recognition by PNA Hairpins

This example describes the use of hybridization to inhibit electron transfer quenching, demonstrating the ability of PNA/DNA duplexes to act as "bioinsulators".

In this example, sequence specific recognition of ss DNA by PNA hairpins 626 and 627 is demonstrated by thermal denaturation and fluorescence spectroscopy. A similar approach has been reported by Tyagi and Kramer (Tyagi, S.; Kramer, F. R. Nature Biotechnol. 1996, 14, 303–308). In that strategy, a DNA hairpin was labelled with an energy donor and acceptor. Hybridization led to decreased energy transfer between the donor and acceptor. The use of PNA in the present invention rather than DNA is preferred because of the superior hybridization characteristics of PNA, namely the much higher affinity and ionic strength independence of the PNA-DNA recognition. The choice of electron transfer rather than energy transfer in the present invention arises from the fact that fewer restrictions are placed on the donor and acceptor moieties for photoinduced electron transfer chemistry. In particular, either the donor or acceptor can be irradiated and there is no requirement that the donor absorb light of shorter wavelength than the acceptor.

PNA626 and PNA627 are shown below in their extended and folded conformations. PNA626 contains an acridine moiety ($R_2$) which functions as a light absorber and electron donor plus an anthraquinone moiety ($Q_1$) which functions as an electron acceptor. In the folded conformation, the acridine and quinone will be placed in close proximity to one another, particularly if both are stacked within the helix, leading to efficient photoinduced electron transfer, which is detected by quenching of the acridine fluorescence. PNA627 is analogous to PNA626 except it lacks the quinone acceptor. A thymine is included in place of the quinone, leading to a T—T mismatch in the folded conformation.

PNA626: H-A-T-A-T-Q-T-T-G-G-C-T-G-A-T-C-C-A-R2-T-A-T-A-T-Lys-Lys-NH$_2$ (SEQ ID NO:3)

PNA627: H-A-T-A-T-T-T-T-G-G-C-T-G-A-T-C-C-A-R$_2$-T-A-T-A-T-Lys-Lys-NH$_2$ (SEQ ID NO:4)

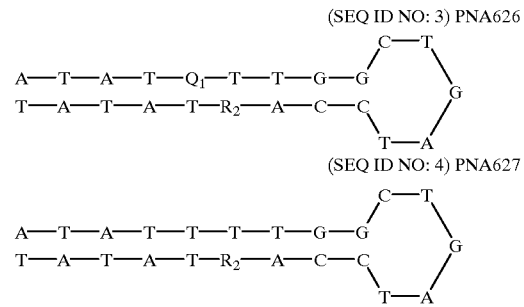

DNA Targets (single stranded, linear)

626A: 5'-T-G-G-A-T-C-A-G-C-C-A-A-3' (SEQ ID NO:5)

626B: 5'-T-G-G-A-T-C-A-G-C-C-T-A-3' (SEQ ID NO:6)

626C: 5'-T-G-G-A-T-C-T-G-C-C-A-A-3' (SEQ ID NO:7)

626D: 5'-A-T-A-T-A-T-T-G-G-A-T-C-A-G-C-C-A-A-T-A-T-A-T-3' (SEQ ID NO:8)

626A is perfectly complementary to the 12 base sequence separating the quinone from the acridine. 626B and 626C will hybridize with the PNAs but with single base mismatches. The mismatch for 626B will be located near the end of the resulting duplex, yielding a 10 base pair segment, whereas the mismatch for 626C will be located near the center of the resulting duplex, yielding 6 and 5 base pair segments. 626D will hybridize with the full length of the PNAs, placing thymines across from the acridine and quinone moieties.

Thermal Denaturation Experiments

Samples were prepared containing 2.5 $\mu$M PNA in 10 mM sodium phosphate buffer (pH=7.0) with and without 2.5 $\mu$M DNA626A. Melting curves were recorded by monitoring the absorbance at 260 nm over the temperature range 25–90° C.

Figure 16:
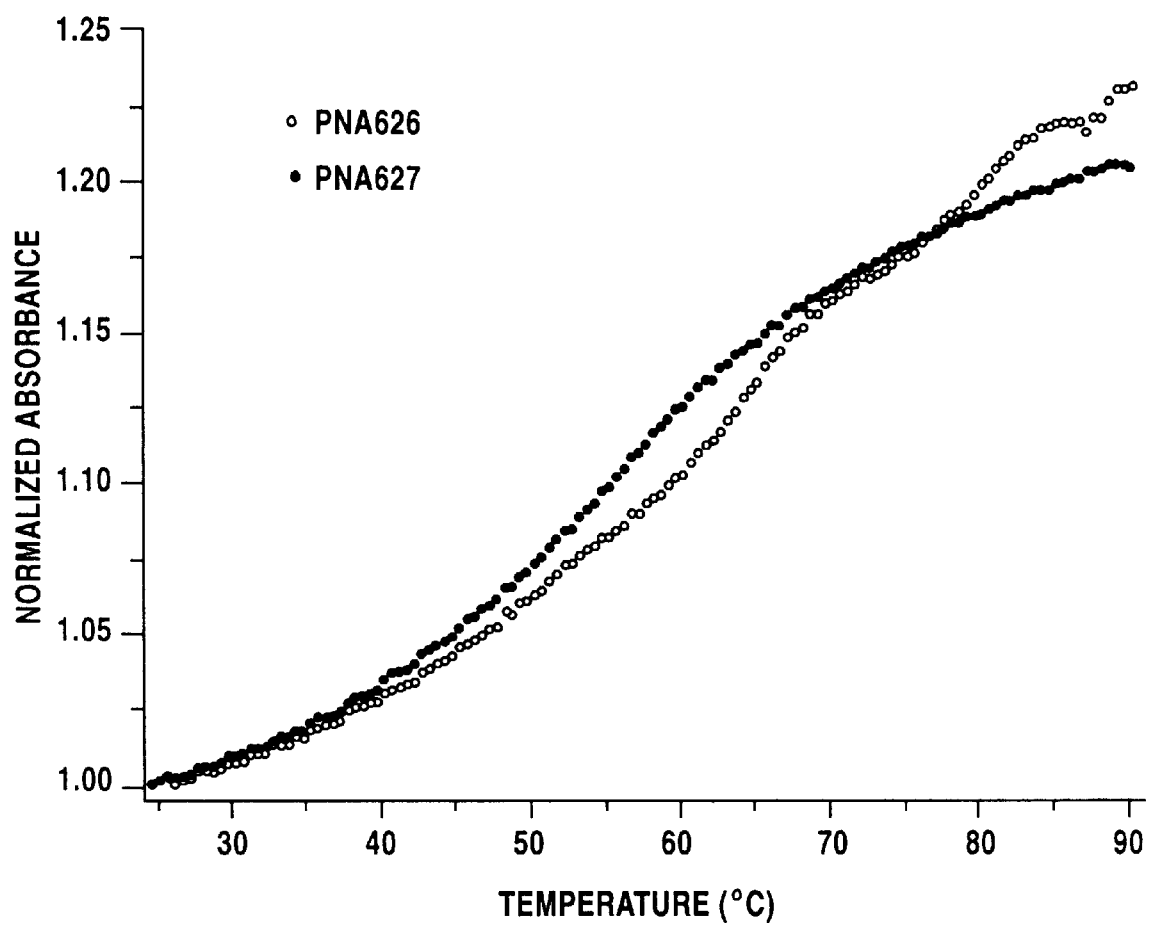
FIG. 16 shows absorbance/temperature profiles for PNA626 and 627 hairpins.

FIG. 16 shows the curves for melting of the PNAs in the absence of DNA. The substantial hyperchromicity (>20%) is consistent with a folded hairpin structure rather than an extended linear conformation. The transition midpoint is approximately 55° C. for PNA627. Melting is more complex for PNA626 but the transition to the extended conformation occurs within the range 55–65° C.

Figure 17:
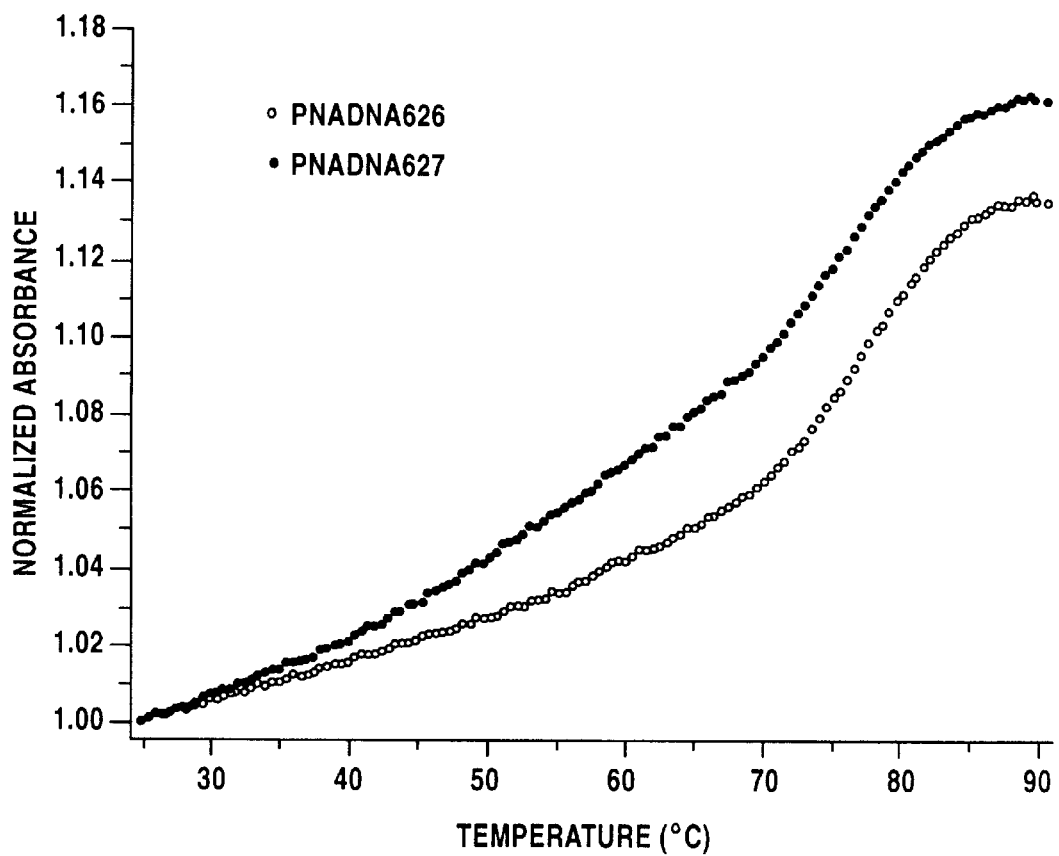
FIG. 17 shows absorbance/temperature profiles for DNA626A hybrids with PNA626 and PNA627.

FIG. 17 shows the curves for melting of the PNAs in the presence of DNA626A. The fact that the two curves in this figure are significantly different from those in FIG. 1 demonstrates that the PNA and DNA strands are interacting with one another. A clear transition is observed at ca. 76° C. for both PNAs. This transition is attributed to melting of the desired PNA/DNA hybrids.

Fluorescence Experiments

Samples were prepared containing 1.0 $\mu$M PNA in 10 mM sodium phosphate buffer (pH=7.0) with and without 1.0 $\mu$M DNA. Samples were heated to 90° C. for 5 min, then cooled to room temperature over a period of 90 minutes. Fluorescence emission spectra were recorded over the range 430–600 nm with excitation at 417 nm. 2.5 mm slits, 1.0 nm increment and 0.5 sec integration time were used for data collection. After collection, spectra were integrated to give the data shown below.

TABLE 3

Effect of Hybridization on ET Quenching of Acridine Fluorescence

| Sample | PNA | DNA | Raw Data | Normalized Data* |
|---|---|---|---|---|
| 1 | 626 | None | 3.35 | 1.00 |
| 2 | 626 | 626A | 12.0 | 3.58 |
| 3 | 626 | 626B | 11.0 | 3.28 |
| 4 | 626 | 626C | 9.98 | 2.98 |
| 5 | 626 | 626D | 25.1 | 7.49 |
| 6 | 627 | None | 12.1 | 1.00 |
| 7 | 627 | 626A | 16.5 | 1.37 |
| 8 | 627 | 626B | 16.4 | 1.36 |
| 9 | 627 | 626C | 15.2 | 1.26 |
| 10 | 627 | 626D | 32.3 | 2.67 |

*Data for each PNA were normalized to the values for the samples lacking DNA (1 and 6).

Effect of Quinone in PNA Hairpin

Comparing samples 1 and 6, the fluorescence is 3.6 times lower when the quinone is present, consistent with quenching of the acridine fluorescence by electron transfer to the adjacent quinone. The lack of complete quenching is most likely due to the fact that the electron transfer reaction is not very favorable energetically and the lifetime of the acridine is probably fairly short (a few nanoseconds). An additional factor, indicated by the broad hairpin melting curves, is that the acridine and quinone likely have multiple conformations (e.g. Intercalated or extrahelical). The incomplete quenching could arise from a population of hairpins in which only one of the two chromophores is actually intercalated at the time of excitation.

Effect of Hybridization

In the presence of complementary DNA, the hairpin is disrupted and a PNA/DNA hybrid is formed. In the hybrid, the acridine and anthraquinone are separated by 12 base pairs instead of being in contact in the hairpin. This results in a substantial increase in the fluorescence (compare samples 1 and 2). The increase is much greater for PNA626 than for 627, indicating that most of the enhanced fluorescence results from retarded electron transfer rather than from the change in the environment of the acridine fluorophore due to hybridization with the DNA strand. Note that the fluorescence is still greater for PNA627, suggesting that there is still some electron transfer quenching occurring over 12 base pairs within the hybrid.

Effect of Single Base Mismatches

A single mismatch near the end of the recognition site results in a 12% decrease in fluorescence enhancement while a mismatch near the center of the recognition site results in a 23% decrease in fluorescence enhancement. As expected, the central mismatch results in shorter (and, therefore, less stable) hybrid regions, leading to less fluorescence enhancement.

Effect of Full-Length Hybridization

The largest enhancements results from hybridization with a full length DNA complement (DNA626D, see Samples 5 and 10). This result emphasizes the sensitivity of the acridine fluorescence quantum yield to its environment: the emission is significantly greater when the acridine is part of a duplex as opposed to in a single strand. (The results for PNA627 also indicate that the acridine fluorescence quantum yield is greater for a PNA-DNA versus a PNA-PNA hybrid. The fluorescence increases by 2.67 in the presence of DNA.) The combination of this effect with the relieved electron transfer results in the large enhancement of fluorescence.

Assessment

The donor-acceptor PNA hairpins appear to work as designed and significant enhancements of fluorescence arise from hybridization with all four DNA oligomers. In each case, the fluorescence was enhanced 2.4–2.8 times more for PNA626 than for PNA627, demonstrating the importance of the electron acceptor in the system. The experiments were performed on samples containing 1 nanomole each of PNA and DNA target; this could easily be decreased by a factor of 10.

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 10
        (D) OTHER INFORMATION: /note= "Position 10 may be an
            abasic nucleic acid."

(xi) SEQUENCE DESCRIPTION: SEQ ID NO:1:

TCGCTGGAAN AAGGTAGGA                                            19

(2) INFORMATION FOR SEQ ID NO:2:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Peptide Nucleic Acid"

(ix) FEATURE:
        (A) NAME/KEY: misc_feature
        (B) LOCATION: 9..10
        (D) OTHER INFORMATION: /note= "Between position 9 and position
            10 there is eithe an acetyl, a 3,6-Diaza-
            (N3-2-anthraquinoyl)-N6-boc-hexanoic acid, or a
            3,6-Diaza(N3-boc-aminoethyl)-4,7-dioxo-7
            -(2-anthraquinyl)-heptanoic acid.

(ix) FEATURE:
        (A) NAME/KEY: misc_feature
        (B) LOCATION: 1
        (D) OTHER INFORMATION: /note= "Position 1 has an H-Lys-Lys
            substituent."

(ix) FEATURE:
        (A) NAME/KEY: misc_feature
        (B) LOCATION: 18
        (D) OTHER INFORMATION: /note= "Postion 18 has a Gly-NH2
            substituent."

(xi) SEQUENCE DESCRIPTION: SEQ ID NO:2:

TCCTACCTTT TCCAGCGA                                            18

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: both
        (D) TOPOLOGY: both (ii) MOLECULE TYPE: other nucleic acid
        (A) DESCRIPTION: /desc = "Peptide Nucleic Acid"

(ix) FEATURE:
        (A) NAME/KEY: misc_feature
        (B) LOCATION: 1
        (D) OTHER INFORMATION: /note= "Position 1 is either
            unsubstituted or has an H- substituent."

(ix) FEATURE:
        (A) NAME/KEY: misc_feature (B) LOCATION: 4..5
            (D) OTHER INFORMATION: /note= "Between positions 4 and 5 is an
                anthraquinone moiety."

(ix) FEATURE:
            (A) NAME/KEY: misc_feature
            (B) LOCATION: 16..17
            (D) OTHER INFORMATION: /note= "Between positions 16 and 17 is
                an acridine moiety."

(ix) FEATURE:
            (A) NAME/KEY: misc_feature
            (B) LOCATION: 21
            (D) OTHER INFORMATION: /note= "Position 21 is either
                unsubstitued or has a Lys-Lys-NH2 substituent."

(xi) SEQUENCE DESCRIPTION: SEQ ID NO:3:

ATATTTGGCT GATCCATATA T                                          21

(2) INFORMATION FOR SEQ ID NO:4:

(i) SEQUENCE CHARACTERISTICS:
            (A) LENGTH: 22 base pairs
            (B) TYPE: nucleic acid
            (C) STRANDEDNESS: both
            (D) TOPOLOGY: both (ii) MOLECULE TYPE: other nucleic acid
            (A) DESCRIPTION: /desc = "Peptide Nucleic Acid"

(ix) FEATURE:
            (A) NAME/KEY: misc_feature
            (B) LOCATION: 1
            (D) OTHER INFORMATION: /note= "Position 1 is either
                unsubstituted or has an -H substituent."

(ix) FEATURE:
            (A) NAME/KEY: misc_feature
            (B) LOCATION: 17..18
            (D) OTHER INFORMATION: /note= "Between positions 17 and 18
                is an acridine moiety."

(ix) FEATURE:
            (A) NAME/KEY: misc_feature
            (B) LOCATION: 22
            (D) OTHER INFORMATION: /note= "Position 22 is either
                unsubstituted or has a Lys-Lys-NH2 substituent."

(xi) SEQUENCE DESCRIPTION: SEQ ID NO:4:

ATATTTTGGC TGATCCATAT AT                                         22

(2) INFORMATION FOR SEQ ID NO:5:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

TGGATCAGCC AA                                                    12

(2) INFORMATION FOR SEQ ID NO:6:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:6:

TGGATCAGCC TA                                               12

(2) INFORMATION FOR SEQ ID NO:7:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TGGATCTGCC AA                                               12

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

ATATATTGGA TCAGCCAATA TAT                                   23

What is claimed is:

1. A molecule of formula VIIIa, VIIIb or VIIIc

VIIIa:

$$E{-}J{-}B(-A-L)(-D-F)$$

or

VIIIb:

$$E{-}J{-}B(-A-L)(-D-E)$$

or

VIIIc:

$$F{-}J{-}B(-A-L)(-D-F)$$

wherein

A is a group of formula I/A, I/B, I/C or I/D

Formula I/A $$\left[\begin{array}{c}R^1\\|\\C\\|\\R^2\end{array}\right]_p - Y - \left[\begin{array}{c}R^1\\|\\C\\|\\R^2\end{array}\right]_q$$

Formula I/B $$\left[\begin{array}{c}R^1\\|\\C\\|\\R^2\end{array}\right]_r - Y - \left[\begin{array}{c}R^1\\|\\C\\|\\R^2\end{array}\right]_s \overset{X}{\underset{\|}{C}}{-}$$

Formula I/C $$\left[\begin{array}{c}R^1\\|\\C\\|\\R^2\end{array}\right]_r - Y - \left[\begin{array}{c}R^1\\|\\C\\|\\R^2\end{array}\right]_s \overset{R^3}{\underset{|}{N}} \overset{O}{\underset{\|}{C}}{-}$$

Formula I/D $$\left[\begin{array}{c}R^1\\|\\C\\|\\R^2\end{array}\right]_r - Y - \left[\begin{array}{c}R^1\\|\\C\\|\\R^2\end{array}\right]_s \overset{X}{\underset{\|}{C}} \overset{R^3}{\underset{|}{N}}{-}$$

wherein

X is selected from the group consisting of O, S, Se, $NR^3$, $CH_2$ and $C(CH_3)_2$;

Y is selected from the group consisting of a single bond, O, S and $NR^4$;

each of p and q is independently 0–5;

each of r and s is independently 0–5;

each of $R^1$ and $R^2$ is independently selected from the group consisting of hydrogen, $C_1$–$C_4$ alkyl which is unsubstituted or substituted by a substituent selected from the group consisting of hydroxy, $C_1$–$C_4$ alkoxy and $C_1$–$C_4$ alkylthio, hydroxy, $C_1$–$C_4$ alkoxy, $C_1$–$C_4$ alkylthio, amino and halogen; and $R^3$ is selected from the group consisting of hydrogen, $C_1$–$C_4$ alkyl which is unsubstituted or substituted by a substituent selected from the group consisting of hydroxy, $C_1$–$C_6$ alkoxy and $C_1$–$C_6$ alkylthio, hydroxy, $C_1$–$C_6$ alkoxy, $C_1$–$C_6$ alkylthio and amino;

B is N or CH;

J is selected from the group consisting of (a) $(CR^6R^7)_y$, wherein (1) $R^6$ is hydrogen and $R^7$ is a side chain of a naturally occurring a-amino acid, (2) $R^6$ and $R^7$ are each independently selected from the group consisting of hydrogen, $C_1$–$C_6$ alkyl, aryl, aralkyl, heteroaryl, hydroxy, $C_1$–$C_6$ alkoxy, $C_1$–$C_6$ alkylthio, $NR^3R^4$ wherein $R^3$ is as defined above and $R^4$ is independently selected from the group consisting of hydrogen, $C_1$–$C_4$ alkyl which is unsubstituted or substituted by a substituent selected from the group consisting of hydroxy, $C_1$–$C_6$ alkoxy and $C_1$–$C_6$ alkylthio, hydroxy, $C_1$–$C_6$ alkoxy, $C_1$–$C_6$ alkylthio and amino, and $SR_5$ wherein $R_5$ is selected from the group consisting of hydrogen, hydroxy, $C_1$–$C_6$ alkoxy and $C_1$–$C_6$ alkyl which is unsubstituted or substituted by $C_1$–$C_6$ alkylthio, or (3) $R^6$ and $R^7$, taken together with the atoms to which they are attached, form an alicyclic or heterocyclic ring system; (b) CO; (c) CS; and (d) $CNR_3$, wherein $R^3$ is as defined above;

D is $CR^6R^7$, wherein $R^6$ and $R^7$ are as defined above;

E is selected from the group consisting of COOH, CSOH, SOOH and $SO_2OH$, or a protected and/or activated derivative thereof;

F is $NHR^3$ or $NPgaR^3$ wherein $R^3$ is as defined above and Pga is an amino protecting group; and L is a non-nucleobase electron donor or acceptor moiety which is capable of participating in the complete transfer of an electron, wherein any amino group in A, B, J and D is unprotected or protected by an amino protecting group.

2. The molecule of claim 1, wherein L is a group of formula IIIa or IIIb

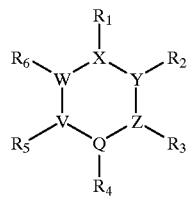

IIIa

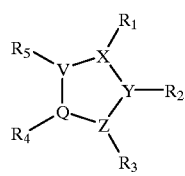

IIIb wherein

X, Y, Z, Q, V and W are each independently selected from the group consisting of C, N, S and O atoms, and X, Y, Z, Q, V and W are each independently connected by single or double bonds and at least one of X, Y, Z, Q, V and W, together with the moiety to which it is bound, may also be selected from the group consisting of —CO—, —SO— and —$SO_2$—; and $R_1$–$R_6$ are each independently selected from the group consisting of (a) hydrogen, (b) oxygen, (c) hydroxy, (d) —OR', (e) —SH, (f) —SR', (g) —$NH_2$, (h) —$NO_2$, (i) —$SO_3^-$, (j) —$SO_2^-$, (k) —CN, (l) $PO_3^{2-}$, (m) $PO_2^-$, (n) —COOH, (o) —COR', (p) —COOR', (q) —CSR', (r) —CSOR', (s) —COO—, (t) —N=N—, (u) halogen, (v) —NHR', (w) N(R'R"), (x) hydrocarbyl wherein the hydrocarbyl is selected from the group consisting of (1) $C_1$–$C_{10}$ alkyl, (2) $C_1$–$C_{10}$ alkenyl, (3) $C_1$–$C_{10}$ alkynyl and (4) a single or fused aryl having 6–30 carbon atoms, wherein any of groups (1)–(4) are uninterrupted or interrupted by at least one heteroatom selected from the group consisting of —N—, —NH—, —S— and —O— and the hydrocarbyl is unsubstituted or substituted at least once by $R_1$, wherein $R_1$ is as described above, (y) a heterocyclic aromatic or non-aromatic moiety containing at least one heteroatom each independently selected from the group consisting of —N—, —NH—, —S— and —O— which is unsubstituted or substituted at least once by $R_1$, wherein $R_1$ is as described above, and (z) a bond, wherein R' and R" are selected from the possible definitions of $R_1$–$R_6$ as described above, wherein at least one of the groups $R_1$–$R_6$ is modified such that the group is capable of binding to the linker, with the proviso that the group of formula IIIa or IIIb is a non-nucleobase moiety.

3. The molecule of claim 2, wherein the heterocyclic aromatic or non-aromatic moiety as $R_1$–$R_6$ is selected from the group consisting of pyridyl, imidazolyl, pyradazinolyl, quinolyl, acridinolyl, pyrrolyl, furyl, thienyl, isoxazolyl, oxazolyl and thiazolyl.

4. The molecule of claim 2, wherein the single or fused aryl having 6–30 carbon atoms as $R_1$–$R_6$ is selected from the group consisting of phenyl, naphthyl, biphenyl, tolyl and anthracenyl, or fused combinations of the group.

5. The molecule of claim 1, wherein L is of formula IVa, IVb, IVc, IVd, or IVe,

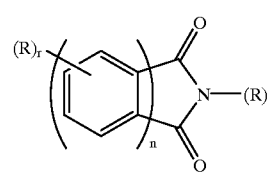

IVa

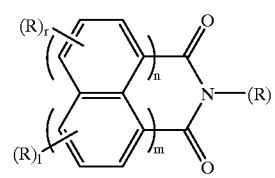

IVb

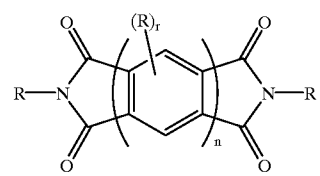

IVc

IVd

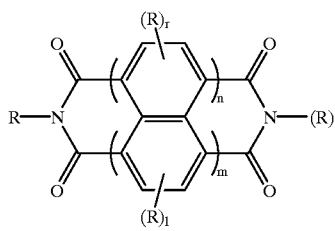

IVe

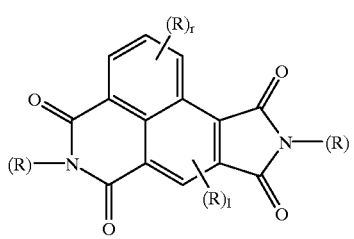

wherein R in each case is selected from the group consisting of (a) hydrogen, (b) oxygen, (c) hydroxy, (d) —OR', (e) —SH, (f) —SR', (g) —NH$_2$, (h) —NO$_2$, (i) —SO$_3^-$, (j) —SO$_2^-$, (k) —CN, (l) —PO$_3^{2-}$, (M) —PO$_2^-$, (n) —COOH, (o) —COR', (p) —COOR', (q) —CSR', (r) —CSOR', (s) —COO—, (t) —N=N—, (u) halogen, (V) —NHR', (w) N(R'R"), (x) hydrocarbyl wherein the hydrocarbyl is selected from the group consisting of (1) C$_1$–C$_{10}$ alkyl, (2) C$_1$–C$_{10}$ alkenyl, (3) C$_1$–C$_{10}$ alkynyl and (4) a single or fused aryl having 6–30 carbon atoms, wherein any of groups (1)–(4) are uninterrupted or interrupted by at least one heteroatom selected from the group consisting of —N—, —NH—, —S— and —O— and the hydrocarbyl is unsubstituted or substituted at least once by R, wherein R is as described above, (y) a heterocyclic aromatic or non-aromatic moiety containing at least one heteroatom each independently selected from the group consisting of —N—, —NH—, —S— and —O— which is unsubstituted or substituted at least once by R, wherein R is as described above, and (z) a bond, wherein R' and R" are selected from the possible definitions of R as described above, wherein at least one of the groups-R in each case is modified such that the group is capable of binding to the linker, n and m are each independently 0 or an integer from 1 to 10, and k, r and l are each independently 0 or an integer from 1 to 4.

6. The molecule of claim 1, wherein L is of formula Va, Vb, Vc or Vd,

Va

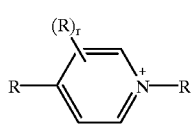

Vb

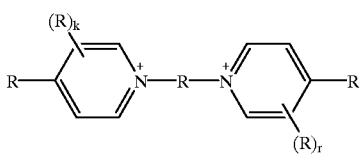

Vc

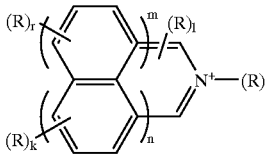

Vd

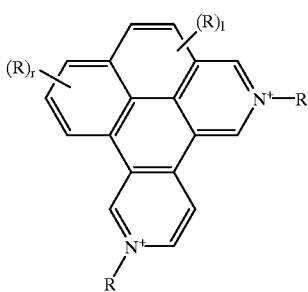

wherein R in each case is selected from the group consisting of (a) hydrogen, (b) oxygen, (c) hydroxy, (d) —OR', (e) —SH, (f) —SR', (g) —NH$_2$, (h) —NO$_2$, (i) —SO$_3^-$, (j) —SO$_2^-$, (k) —CN, (l) —PO$_3^{2-}$, (m) —PO$_2^-$, (n) —COOH, (o) —COR', (p) —COOR', (q) —CSR', (r) —CSOR', (s) —COO—, (t) —N=N—, (u) halogen, (v) —NHR', (w) N(R'R"), (x) hydrocarbyl wherein the hydrocarbyl is selected from the group consisting of (1) C$_1$–C$_{10}$ alkyl, (2) C$_1$–C$_{10}$ alkenyl, (3) C$_1$–C$_{10}$ alkynyl and (4) a single or fused aryl having 6–30 carbon atoms, wherein any of groups (1)–(4) are uninterrupted or interrupted by at least one heteroatom selected from the group consisting of —N—, —NH—, —S— and —O— and the hydrocarbyl is unsubstituted or substituted at least once by R, wherein R is as described above, (y) a heterocyclic aromatic or non-aromatic moiety containing at least one heteroatom each independently selected from the group consisting of —N—, —NH—, —S— and —O— which is unsubstituted or substituted at least once by R, wherein R is as described above, and (z) a bond, wherein R' and R" are selected from the possible definitions of R as described above, wherein at least one of the groups R in each case is modified such that the group is capable of binding to the linker, n and m are each independently 0 or an integer from 1 to 10, and k, r and l are each independently 0 or an integer from 1 to 4.

7. The molecule of claim 1, wherein L is of formula VIa, VIb or VIc,

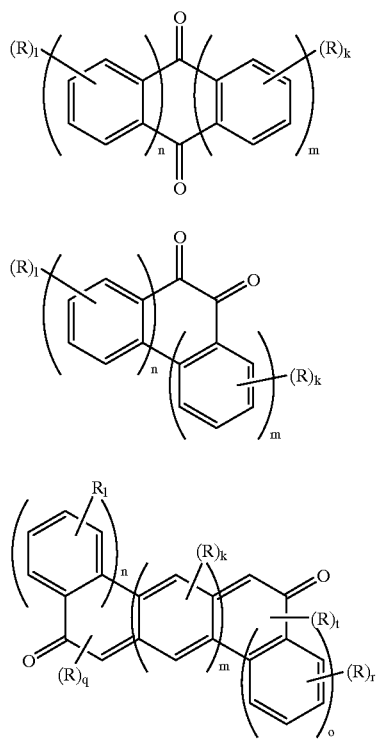

VIa

VIb

VIc

8. The molecule of claim 1, wherein L is of formula VIIa, VIIb or VIIc,

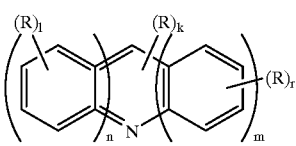

VIIa

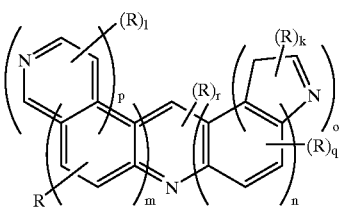

VIIb

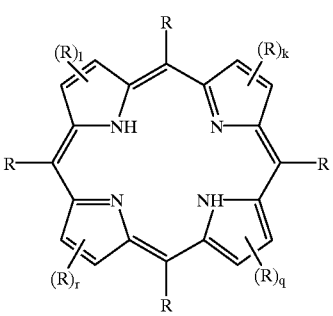

VIIc wherein R in each case is selected from the group consisting of (a) hydrogen, (b) oxygen, (c) hydroxy, (d) —OR', (e) —SH, (f) —SR', (g) —NH$_2$, (h) —NO$_2$, (i) —SO$_3^-$, (j) —SO$_2^-$, (k) —CN, (l) —PO$_3^{2-}$, (m) —PO$_2^-$, (n) —COOH, (o) —COR', (p) —COOR', (q) —CSR', (r) —CSOR', (s) —COO$^-$, (t) —N=N—, (u) halogen, (v) —NHR', (w) N(R'R''), (x) hydrocarbyl wherein the hydrocarbyl is selected from the group consisting of (1) $C_1$–$C_{10}$ alkyl, (2) $C_1$–$C_{10}$ alkenyl, (3) $C_1$–$C_{10}$ alkynyl and (4) a single or fused aryl having 6–30 carbon atoms, wherein any of groups (1)–(4) are uninterrupted or interrupted by at least one heteroatom selected from the group consisting of —N—, —NH—, —S— and —O— and the hydrocarbyl is unsubstituted or substituted at least once by R, wherein R is as described above, (y) a heterocyclic aromatic or non-aromatic moiety containing at least one heteroatom each independently selected from the group consisting of —N—, —NH—, —S— and —O— which is unsubstituted or substituted at least once by R, wherein R is as described above, and (z) a bond, wherein R' and R'' are selected from the possible definitions of R as described above, wherein at least one of the groups R in each case is modified such that the group is capable of binding to the linker, n, m and o are each independently 0 or an integer from 1 to 10, and k, r, l, t and q are each independently 0 or an integer from 1 to 4.

wherein R in each case is selected from the group consisting of (a) hydrogen, (b) oxygen, (c) hydroxy, (d) —OR', (e) —SH, (f) —SR', (g) —NH$_2$, (h) —NO$_2$, (i) —SO$_3^-$, (j) —SO$_2^-$, (k) —CN, (l) —PO$_3^{2-}$, (m) —PO$_2^-$, (n) —COOH, (o) —COR', (p) —COOR', (q) —CSR', (r) —CSOR', (s) —COO$^-$, (t) —N=N—, (u) halogen, (v) —NHR', (w) N(R'R''), (x) hydrocarbyl wherein the hydrocarbyl is selected from the group consisting of (1) $C_1$–$C_{10}$ alkyl, (2) $C_1$–$C_{10}$ alkenyl, (3) $C_1$–$C_{10}$ alkynyl and (4) a single or fused aryl having 6–30 carbon atoms, wherein any of groups (1)–(4) are uninterrupted or interrupted by at least one heteroatom selected from the group consisting of —N—, —NH—, —S— and —O— and the hydrocarbyl is unsubstituted or substituted at least once by R, wherein R is as described above, (y) a heterocyclic aromatic or non-aromatic moiety containing at least one heteroatom each independently selected from the group consisting of —N—, —NH—, —S— and —O— which is unsubstituted or substituted at least once by R, wherein R is as described above, and (z) a bond, wherein R' and R'' are selected from the possible definitions of R as described above, wherein at least one of the groups R in each case is modified such that the group is capable of binding to the linker, n, m, o and p are each independently 0 or an integer from 1 to 10, and k, r, l and q are each independently 0 or an integer from 1 to 4.

9. The molecule of claim 1, wherein the molecule is of formula IX,
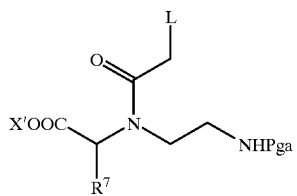
IX
wherein
X' is a carboxylic acid protecting group or hydrogen;
$R^7$ is hydrogen or a side chain of a naturally occurring a-amino acid, or an amino-protected and/or terminal activated derivative thereof; and
L and Pga are as defined above.
* * * * *